US008161585B2

(12) United States Patent
Kuro et al.

(10) Patent No.: US 8,161,585 B2
(45) Date of Patent: *Apr. 24, 2012

(54) PATIENT SUPPORT DEVICE AND METHOD OF OPERATION

(75) Inventors: Serge Nukhim Kuro, Madison, WI (US); Graham T. Reitz, Madison, WI (US); Bradley J. Brunker, Madison, WI (US); Brent Harper, Mazomanie, WI (US)

(73) Assignee: Tomotherapy Incorporated, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/872,288

(22) Filed: Aug. 31, 2010

(65) Prior Publication Data

US 2010/0319128 A1    Dec. 23, 2010

Related U.S. Application Data

(62) Division of application No. 12/204,628, filed on Sep. 4, 2008, now Pat. No. 7,784,127.

(60) Provisional application No. 60/969,904, filed on Sep. 4, 2007.

(51) Int. Cl.
*A47B 13/00* (2006.01)

(52) U.S. Cl. .................... 5/601; 5/611; 5/616; 378/209; 318/375

(58) Field of Classification Search ............... 5/601, 611, 5/616; 378/209, 111, 65, 93; 318/375–381, 318/371–372
See application file for complete search history.

(56) References Cited

U.S. PATENT DOCUMENTS

| 3,348,114 | A |   | 10/1967 | Wright, Jr. et al. |
| 3,497,786 | A |   | 2/1970  | Lombardo |
| 3,675,099 | A | * | 7/1972  | Johnston ....................... 318/378 |
| 3,755,712 | A | * | 8/1973  | DeViney et al. .............. 318/378 |
| 3,851,233 | A | * | 11/1974 | Sherman ....................... 318/375 |
| 3,974,384 | A | * | 8/1976  | Winkler ........................ 378/111 |
| 4,354,112 | A | * | 10/1982 | Nishio .......................... 378/111 |
| 4,987,583 | A | * | 1/1991  | Travanty et al. ................ 378/95 |
| 5,044,354 | A |   | 9/1991  | Goldhorn et al. |
| 5,105,141 | A | * | 4/1992  | Ernest ............................ 378/93 |
| 5,113,420 | A |   | 5/1992  | Davis, Jr. et al. |
| 5,210,893 | A |   | 5/1993  | Uosaki et al. |

(Continued)

FOREIGN PATENT DOCUMENTS

CA         2091275       9/1993

(Continued)

OTHER PUBLICATIONS

Office Action from Chinese Patent Office for Application No. 200880105521.6 dated Feb. 25, 2011.

(Continued)

*Primary Examiner* — Robert G Santos
*Assistant Examiner* — Brittany Wilson
(74) *Attorney, Agent, or Firm* — Michael Best & Friedrich LLP

(57) ABSTRACT

A patient support device of a radiation therapy treatment system includes an electromechanical motor and control system for moving the support device. The control system utilizes regenerative braking concepts, converting the motor into a generator as the support device is moved such that no matter the load, the support device will be moved at a constant speed. The control system also allows for moving of the support device in the powered off situation (i.e., when there is no power to the support device).

18 Claims, 19 Drawing Sheets

U.S. PATENT DOCUMENTS

| | | | |
|---|---|---|---|
| 5,317,616 A | 5/1994 | Swerdloff et al. | |
| 5,351,280 A | 9/1994 | Swerdloff et al. | |
| 5,442,675 A | 8/1995 | Swerdloff et al. | |
| 5,446,548 A | 8/1995 | Gerig et al. | |
| 5,528,650 A | 6/1996 | Swerdloff et al. | |
| 5,548,627 A | 8/1996 | Swerdloff et al. | |
| 5,625,663 A | 4/1997 | Swerdloff et al. | |
| 5,647,663 A | 7/1997 | Holmes | |
| 5,651,043 A | 7/1997 | Tsuyuki et al. | |
| 5,661,773 A | 8/1997 | Swerdloff et al. | |
| 5,751,781 A | 5/1998 | Brown et al. | |
| 5,754,622 A | 5/1998 | Hughes | |
| 5,754,623 A | 5/1998 | Seki | |
| 5,835,562 A | 11/1998 | Ramsdell et al. | |
| 6,094,760 A * | 8/2000 | Nonaka et al. | 5/601 |
| 6,442,777 B1 | 9/2002 | Pauli | |
| 6,637,056 B1 | 10/2003 | Tybinkowski et al. | |
| 6,653,806 B1 * | 11/2003 | Ono | 318/378 |
| 6,769,145 B1 | 8/2004 | Pfeuffer et al. | |
| 6,857,147 B2 * | 2/2005 | Somasundaram | 5/601 |
| 6,906,493 B1 * | 6/2005 | Ramirez et al. | 318/378 |
| 6,955,464 B1 | 10/2005 | Tybinkowski et al. | |
| 7,008,105 B2 | 3/2006 | Amann et al. | |
| 7,028,356 B2 | 4/2006 | Somasundaram | |
| 7,552,490 B2 * | 6/2009 | Saracen et al. | 5/601 |
| 2003/0107349 A1 * | 6/2003 | Haydock et al. | 322/28 |
| 2003/0222617 A1 | 12/2003 | Nakai et al. | |
| 2004/0172756 A1 | 9/2004 | Somasundaram | |
| 2005/0114996 A1 * | 6/2005 | Somasundaram | 5/601 |
| 2005/0283911 A1 * | 12/2005 | Roussy | 5/611 |
| 2006/0042009 A1 | 3/2006 | Somasundaram et al. | |
| 2007/0093359 A1 * | 4/2007 | Kobayashi et al. | 477/107 |
| 2007/0107128 A1 * | 5/2007 | Somasundaram et al. | 5/601 |
| 2008/0235873 A1 | 10/2008 | Farooqui | |
| 2008/0279328 A1 | 11/2008 | Zeitler et al. | |
| 2009/0056022 A1 | 3/2009 | Reitz et al. | |
| 2009/0070935 A1 | 3/2009 | Brunker et al. | |
| 2009/0159677 A1 * | 6/2009 | Yakimov et al. | 235/439 |
| 2009/0268491 A1 * | 10/2009 | Wilson | 363/78 |

FOREIGN PATENT DOCUMENTS

| | | |
|---|---|---|
| JP | 11313900 | 11/1999 |
| WO | 2005041835 | 5/2005 |

OTHER PUBLICATIONS

Extended Search Report from European Patent Office for Application No. 08799171.7 dated Apr. 21, 2011.

PCT/US2008/075267 International Search Report and Written Opinion dated Jan. 21, 2009.

* cited by examiner

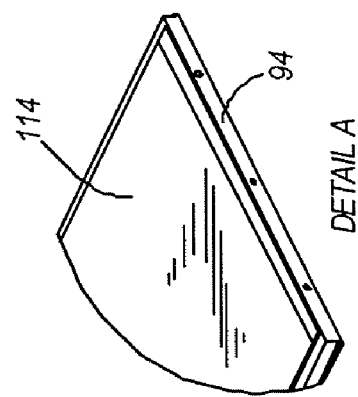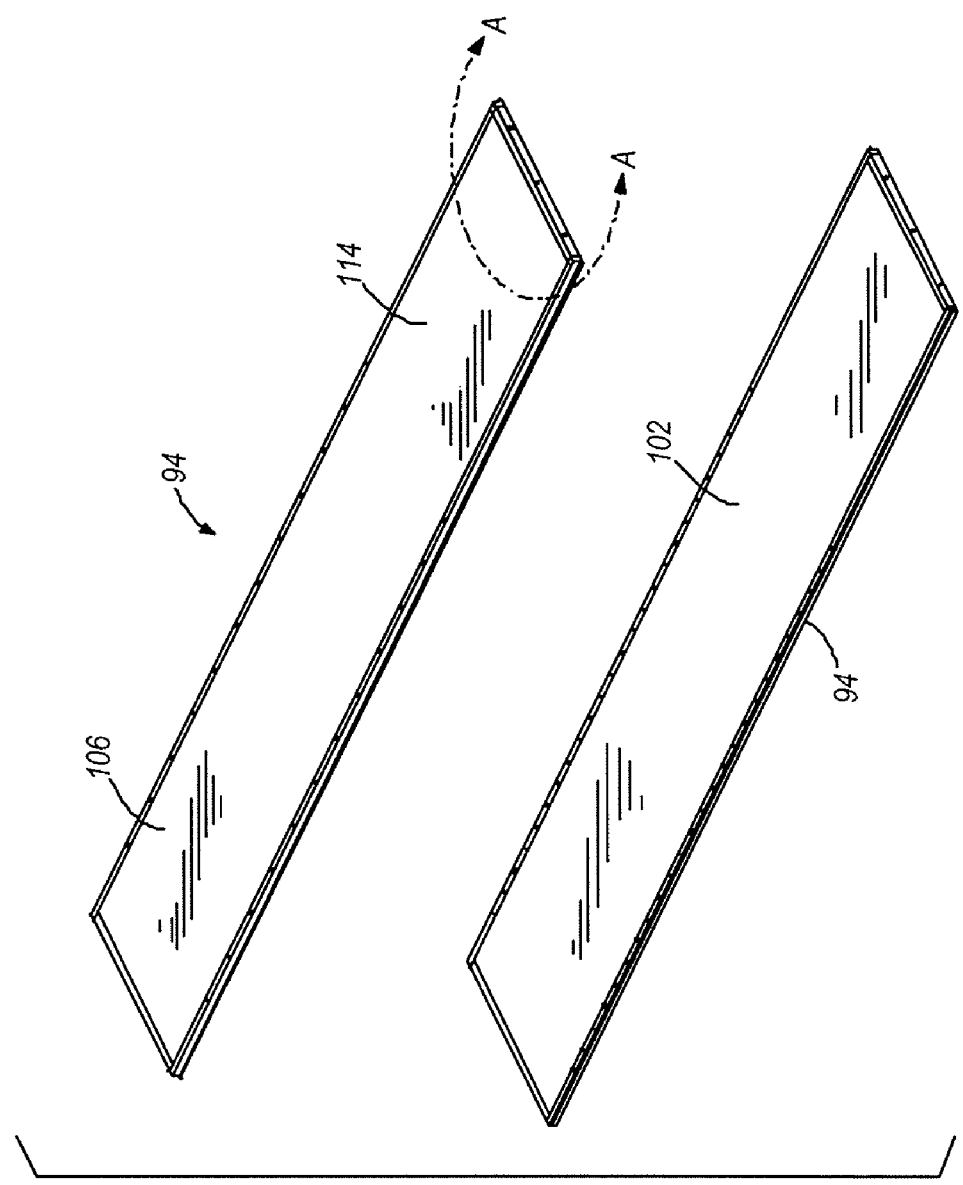
FIG. 5

Condition of the balance between system resistance and external load $$P_{ED}+P_{INT}=P_{EXT}$$

$P_{ED}$ is the system controlled electrodynamic resistance (load)

PATIENT SUPPORT DEVICE AND METHOD OF OPERATION

RELATED APPLICATIONS

This application is a divisional of and claims priority to U.S. patent application Ser. No. 12/204,628 filed on Sep. 4, 2008, which claims priority to U.S. Provisional Patent Application No. 60/969,904, filed on Sep. 4, 2007. The entire contents of each application are incorporated herein by reference.

FIELD OF THE INVENTION

This invention relates to a radiation therapy imaging and treatment system. More specifically, the invention relates to a patient support device for use with such a system.

BACKGROUND OF THE INVENTION

Medical equipment for radiation therapy treats tumorous tissue with high energy radiation. The dose and the placement of the dose must be accurately controlled to ensure both that the tumor receives sufficient radiation to be destroyed, and that damage to the surrounding and adjacent non-tumorous tissue is minimized. Intensity modulated radiation therapy ("IMRT") treats a patient with multiple rays of radiation each of which may be independently controlled in intensity and/or energy. The rays are directed from different angles about the patient and combine to provide a desired dose pattern. In external source radiation therapy, a radiation source external to the patient treats internal tumors. The external source is normally collimated to direct a beam only to the tumorous site. Typically, the radiation source includes either high-energy X-rays, electrons from certain linear accelerators, or gamma rays from highly focused radioisotopes, though other types of radiation sources are possible.

One way to control the position of the radiation delivery to the patient is through the use of a patient support device, such as a couch, that is adjustable in one or more directions. The use of a patient support device is well known in the medical field, with similar patient support devices being used in CT scanning devices and Magnetic Resonances Imagers (MRIs). The patient support device allows the patient to be moved into and out of the field of the radiation to be delivered and in some cases, allow for adjustments of patient position during a radiation treatment.

SUMMARY OF THE INVENTION

When a patient support device, such as a couch, is used in this manner, there are many variables that need to be accounted for. For example construction materials and configuration of suitable electronics necessary to operate the couch must be carefully selected to ensure smooth operation of the couch, and precise measurement of couch position (when the couch has multiple movable parts). When these features are thoughtfully considered in the environment of radiation delivery, the patient support device can be a key tool in improving patient outcomes.

The present invention provides a patient support device comprising a base, a table assembly supported by the base and configured to support a patient, a motor electrically coupled to and operable to control motion of the table assembly, a controller electrically coupled to the motor, the controller operable to generate a signal to brake the motor when power to the motor is interrupted, and a brake control module. The brake control module is electrically coupled to the motor and the controller and is operable upon reactivation of the motor. The brake control module includes a passive dynamic load module electrically coupled to the motor to increase speed of the motor, a rectification module electrically coupled to the motor and operable to convert AC voltage to DC voltage when the AC voltage reaches a predetermined value, a controlled dynamic load module electrically coupled to the passive dynamic load module, and a switch electrically coupled to the controlled dynamic load module and operable to connect and disconnect the controlled dynamic load module to the motor to control a braking operation of the motor.

In another aspect, the present invention provides a radiation therapy treatment system comprising a patient support device and a control system. The patient support device includes a table assembly configured to support a patient, and a motor electrically connected to the table assembly and operable to control movement of the table assembly. The control system is electrically connected to the motor and operable to control a speed of the motor and provide linear motion of the table assembly when power to the couch is interrupted.

Other aspects of the invention will become apparent by consideration of the detailed description and accompanying drawings.

BRIEF DESCRIPTION OF THE DRAWINGS

FIG. 5 is a perspective view of an upper support of the table assembly of FIG. 4.

DETAILED DESCRIPTION

Figure 1:
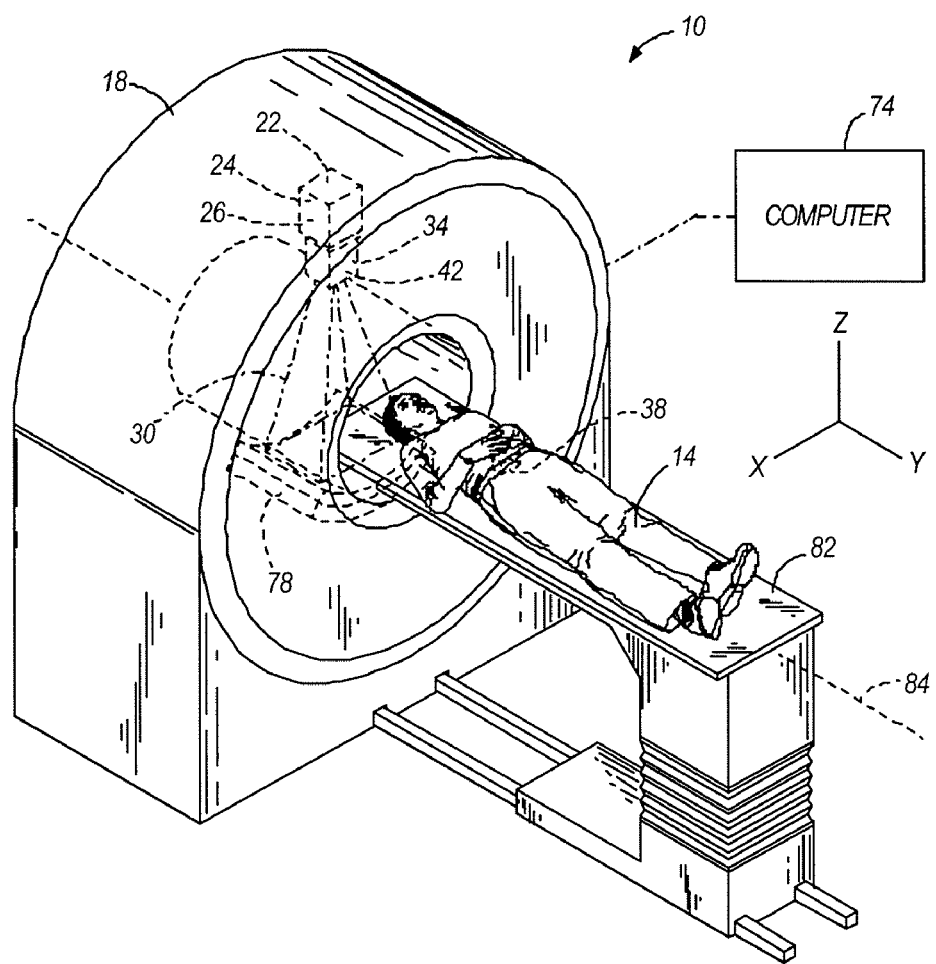
FIG. 1 is a perspective view of a radiation therapy treatment system.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein are for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the present invention in any form. In addition, terms such as "first," "second," and "third" are used herein for purposes of description and are not intended to indicate or imply relative importance or significance.

In addition, it should be understood that embodiments of the invention include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

FIG. 1 illustrates a radiation therapy treatment system 10 that can provide radiation therapy to a patient 14. The radiation therapy treatment can include photon-based radiation therapy, brachytherapy, electron beam therapy, proton, neutron, or particle therapy, or other types of treatment therapy. The radiation therapy treatment system 10 includes a gantry 18. The gantry 18 can support a radiation module 22, which can include a radiation source 24 and a linear accelerator 26 (a.k.a. "a linac") operable to generate a beam 30 of radiation. Though the gantry 18 shown in the drawings is a ring gantry, i.e., it extends through a full 360° arc to create a complete ring or circle, other types of mounting arrangements may also be employed. For example, a C-type, partial ring gantry, or robotic arm could be used. Any other framework capable of positioning the radiation module 22 at various rotational and/or axial positions relative to the patient 14 may also be employed. In addition, the radiation source 24 may travel in path that does not follow the shape of the gantry 18. For example, the radiation source 24 may travel in a non-circular path even though the illustrated gantry 18 is generally circular-shaped. The gantry 18 of the illustrated embodiment defines a gantry aperture 32 into which the patient 14 moves during treatment.

The radiation module 22 can also include a modulation device 34 operable to modify or modulate the radiation beam 30. The modulation device 34 provides the modulation of the radiation beam 30 and directs the radiation beam 30 toward the patient 14. Specifically, the radiation beam 30 is directed toward a portion 38 of the patient. Broadly speaking, the portion 38 may include the entire body, but is generally smaller than the entire body and can be defined by a two-dimensional area and/or a three-dimensional volume. A portion or area desired to receive the radiation, which may be referred to as a target or target region, is an example of a region of interest. Another type of region of interest is a region at risk. If a portion includes a region at risk, the radiation beam is preferably diverted from the region at risk. Such modulation is sometimes referred to as intensity modulated radiation therapy ("IMRT").

Figure 2:
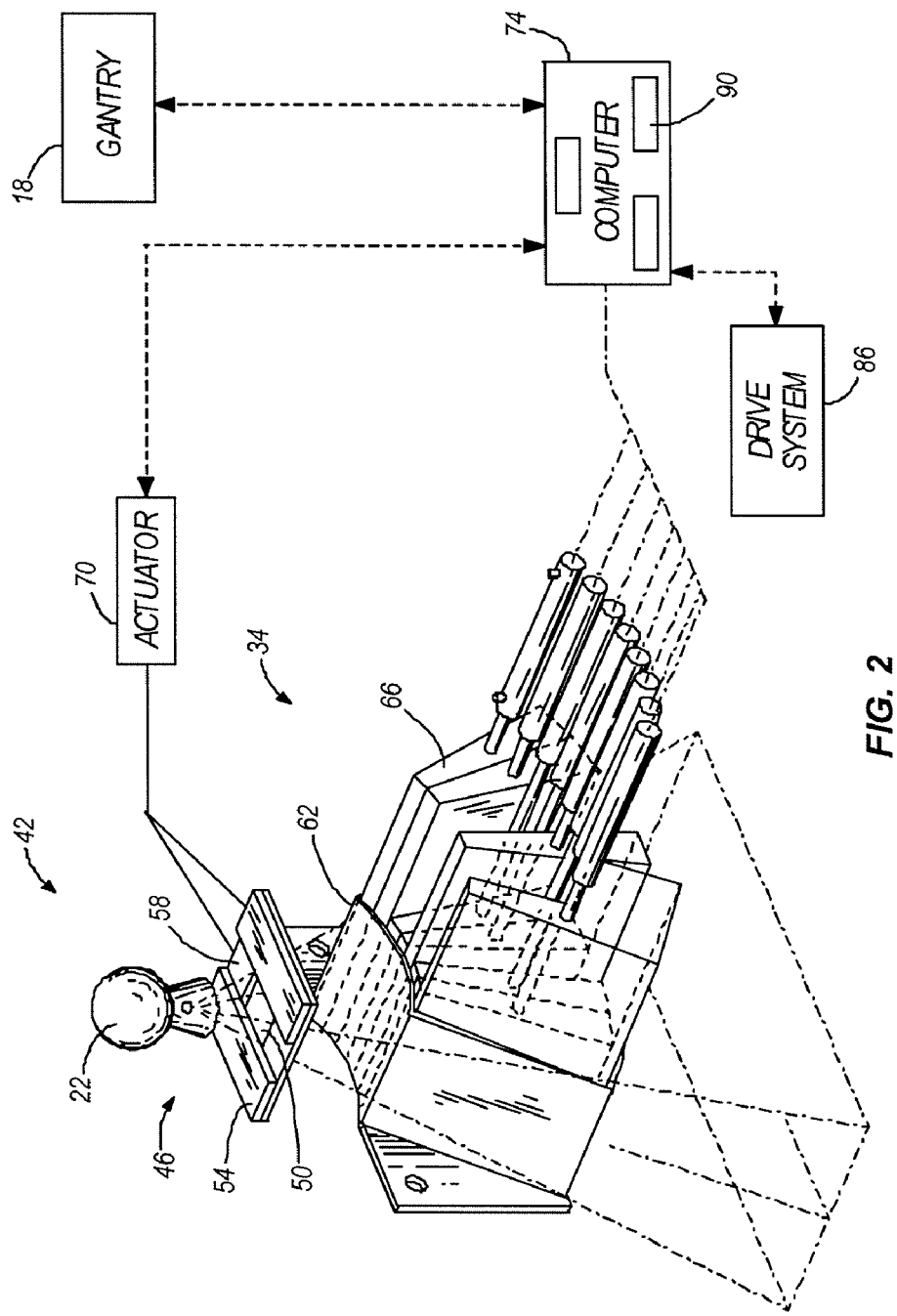
FIG. 2 is a perspective view of a multi-leaf collimator that can be used in the radiation therapy treatment system illustrated in FIG. 1.

The modulation device 34 can include a collimation device 42 as illustrated in FIG. 2. The collimation device 42 includes a set of jaws 46 that define and adjust the size of an aperture 50 through which the radiation beam 30 may pass. The jaws 46 include an upper jaw 54 and a lower jaw 58. The upper jaw 54 and the lower jaw 58 are moveable to adjust the size of the aperture 50. The position of the jaws 46 regulates the shape of the beam 30 that is delivered to the patient 14.

In one embodiment, and illustrated in FIG. 2, the modulation device 34 can comprise a multi-leaf collimator 62 (a.k.a. "MLC"), which includes a plurality of interlaced leaves 66 operable to move from position to position, to provide intensity modulation. It is also noted that the leaves 66 can be moved to a position anywhere between a minimally and maximally-open position. The plurality of interlaced leaves 66 modulate the strength, size, and shape of the radiation beam 30 before the radiation beam 30 reaches the portion 38 on the patient 14. Each of the leaves 66 is independently controlled by an actuator 70, such as a motor or an air valve so that the leaf 66 can open and close quickly to permit or block the passage of radiation. The actuators 70 can be controlled by a computer 74 and/or controller.

The radiation therapy treatment system 10 can also include a detector 78, e.g., a kilovoltage or a megavoltage detector, operable to receive the radiation beam 30, as illustrated in FIG. 1. The linear accelerator 26 and the detector 78 can also operate as a computed tomography (CT) system to generate CT images of the patient 14. The linear accelerator 26 emits the radiation beam 30 toward the portion 38 in the patient 14. The portion 38 absorbs some of the radiation. The detector 78 detects or measures the amount of radiation absorbed by the portion 38. The detector 78 collects the absorption data from different angles as the linear accelerator 26 rotates around and emits radiation toward the patient 14. The collected absorption data is transmitted to the computer 74 to process the absorption data and to generate images of the patient's body tissues and organs. The images can also illustrate bone, soft tissues, and blood vessels.

The system 10 can also include a patient support device, shown as a couch 82, operable to support at least a portion of the patient 14 during treatment. While the illustrated couch 82 is designed to support the entire body of the patient 14, in other embodiments of the invention the patient support need not support the entire body, but rather can be designed to support only a portion of the patient 14 during treatment. The couch 82 moves into and out of the field of radiation along an axis 84 (i.e., Y axis). The couch 82 is also capable of moving along the X and Z axes as illustrated in FIG. 1.

With reference to FIGS. 3-6, the couch 82 includes a table assembly 92 coupled to a base 93 via a platform 95. The table assembly 92 includes an upper support 94 movably coupled to a lower support 98. With particular reference to FIG. 5, the upper support 94 is a substantially flat, rectangular support member on which the patient is supported during treatment. The upper support 94 is movable with respect to the lower support 98 to move the patient into and out of the radiation beam 30 during treatment. In the illustrated embodiment, the upper and lower supports 94, 98 are composed of a carbon fiber composite, though other suitable compositions of the supports are possible.

The upper support 94 includes an upper surface 102 and a lower surface 106 that contacts an upper surface 110 of the lower support 98. As shown in the illustrated embodiment, the lower surface 106 includes a bearing layer 114 that is intended to reduce friction between the lower surface 106 and the upper surface 110 of the lower support 98 when the upper support 94 is moved with respect to the lower support 98. Specific details of the bearing layer 114 and its application are discussed in co-pending U.S. patent application Ser. No. 12/204,617, the entire contents of which are incorporated herein by reference.

The table assembly 92 is movable in the X, Y, and Z directions, as illustrated in FIG. 1. Positioning of the table assembly 92, and thus the position of the patient, with respect to the gantry 18 and the radiation beam 30 must be precise to ensure that the radiation is delivered to the proper areas of the patient. The movement of the table assembly 92 is controlled by the couch operator using a control keypad 140, illustrated in FIGS. 7-10.

Once the user actuates the buttons 144 of the keypad 140, the table assembly 92 will move at the direction of the user. In conventional couch designs, a hydraulic lifting system is utilized to move the table assembly 92 in the Z direction. The hydraulic lifting system is a convenient way to achieve some control over the lowering of the table assembly 92, and has the benefit of allowing the table assembly 92 to be lowered when there is no power delivered to the system 10. When the power to the couch 82 is disrupted while a patient is in the treatment position, the table assembly 92 needs to be lowered to allow the patient to exit the couch, and such lowering must be done in a controlled manner. However, hydraulic systems are more expensive to implement, are less reliable, and are less accurate in their range of motion.

Figure 3:
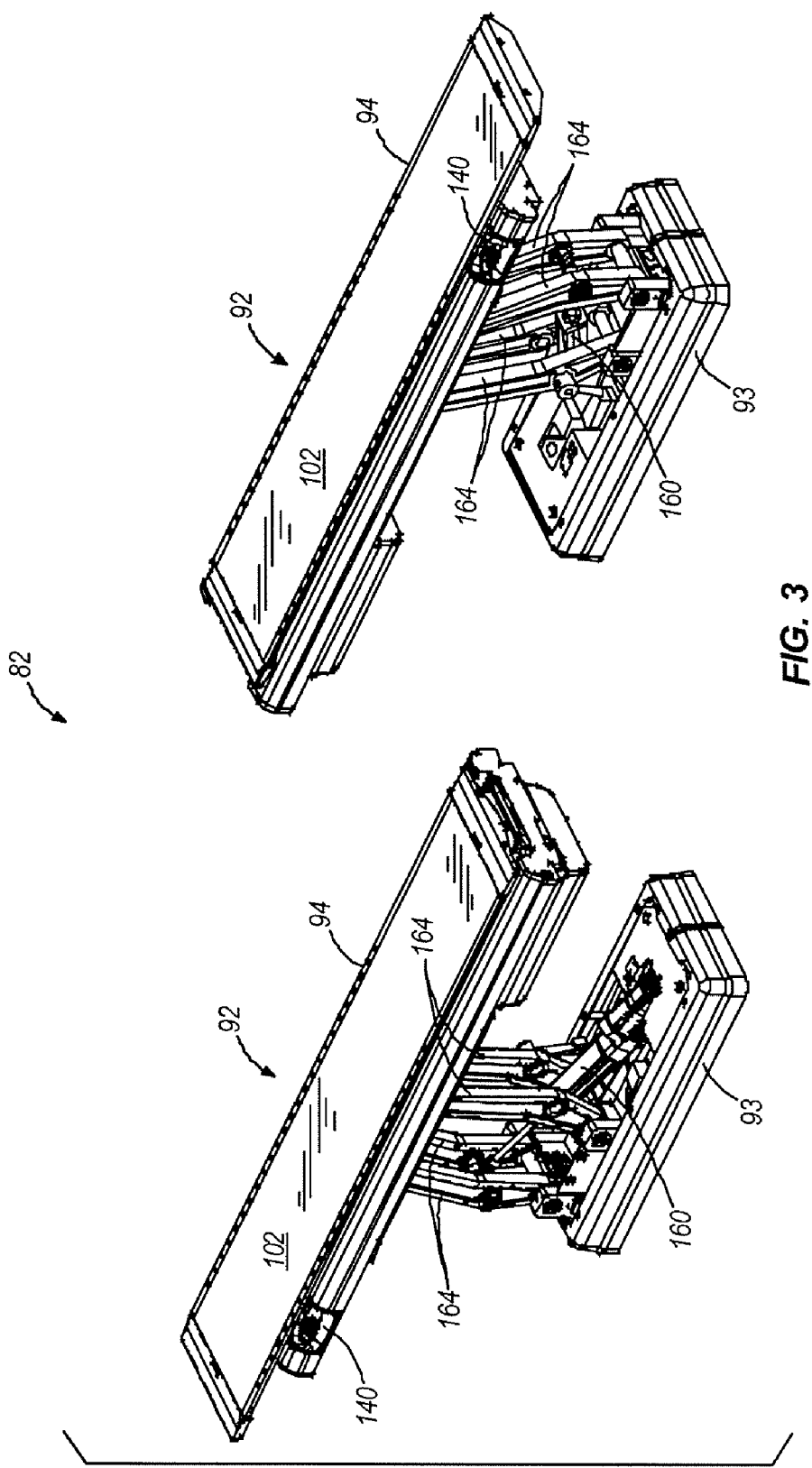
FIG. 3 is a perspective view of a patient support device for use with the system of FIG. 1.
Figure 4:
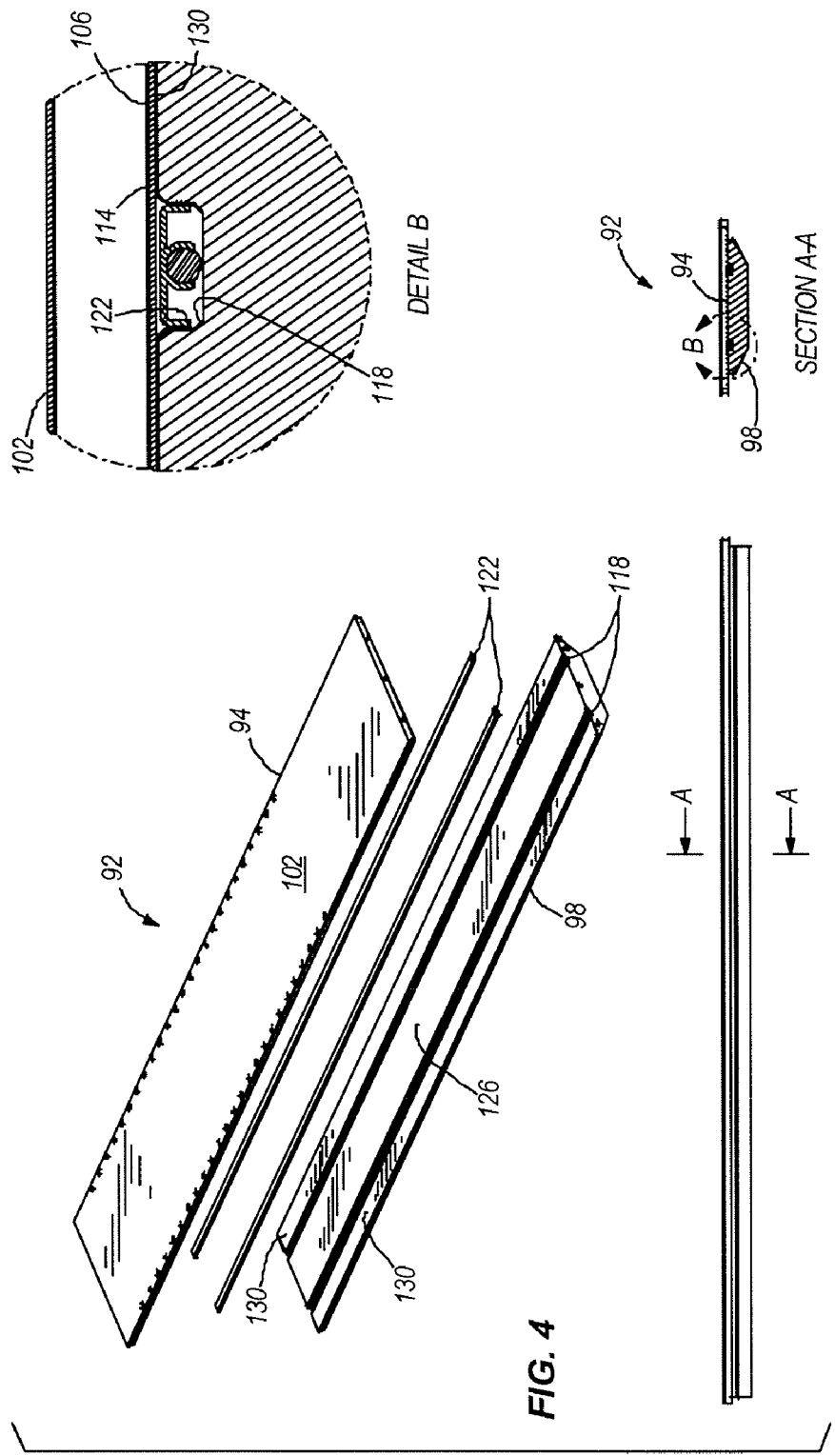
FIG. 4 is an exploded view of a table assembly of the patient support device of FIG. 3.
Figure 6:
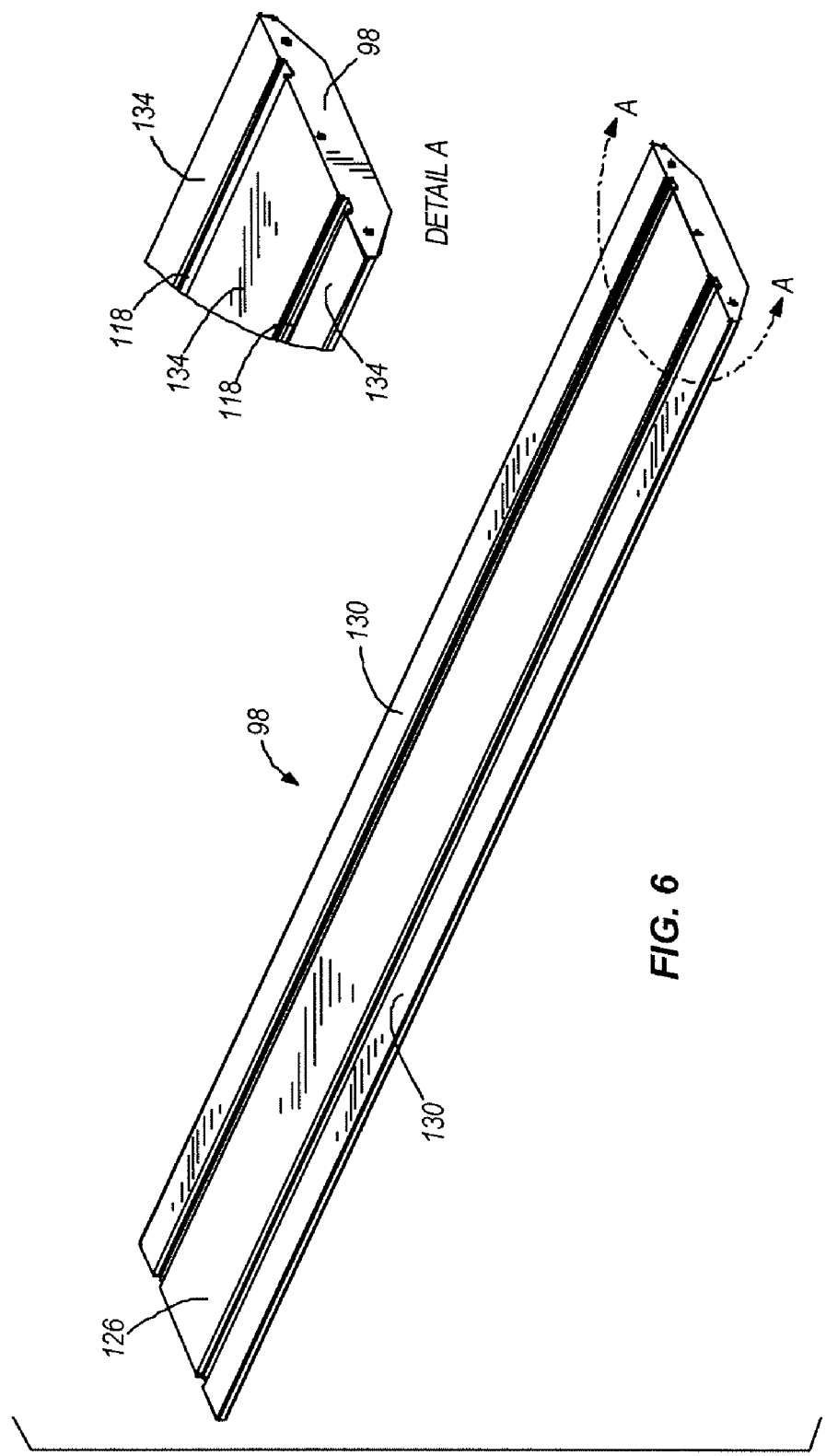
FIG. 6 is a perspective view of a lower support of the table assembly of FIG. 4.
Figure 7:
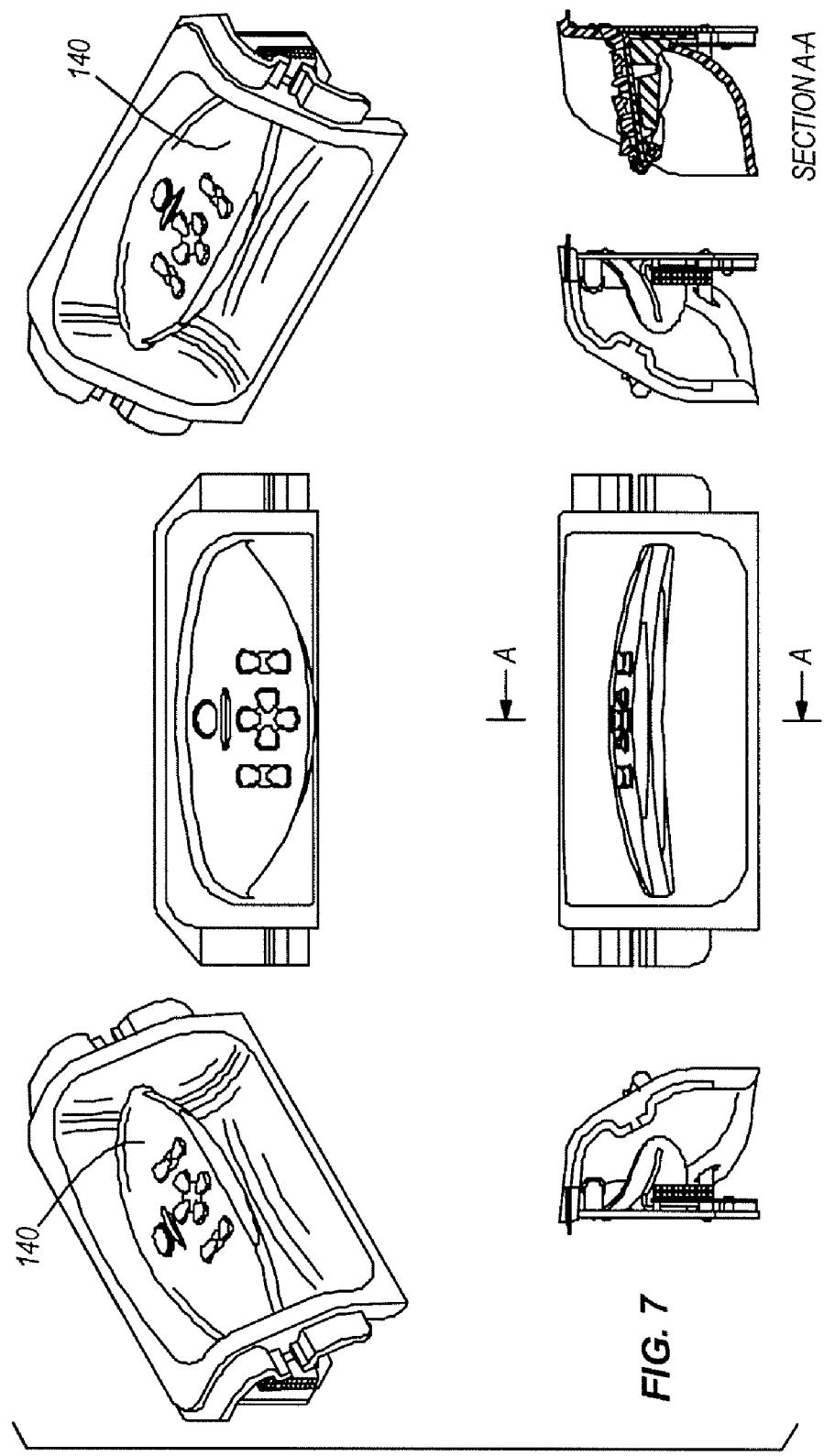
FIG. 7 is an assortment of views of a control keypad for use with the patient support device of FIG. 1.
Figure 8:
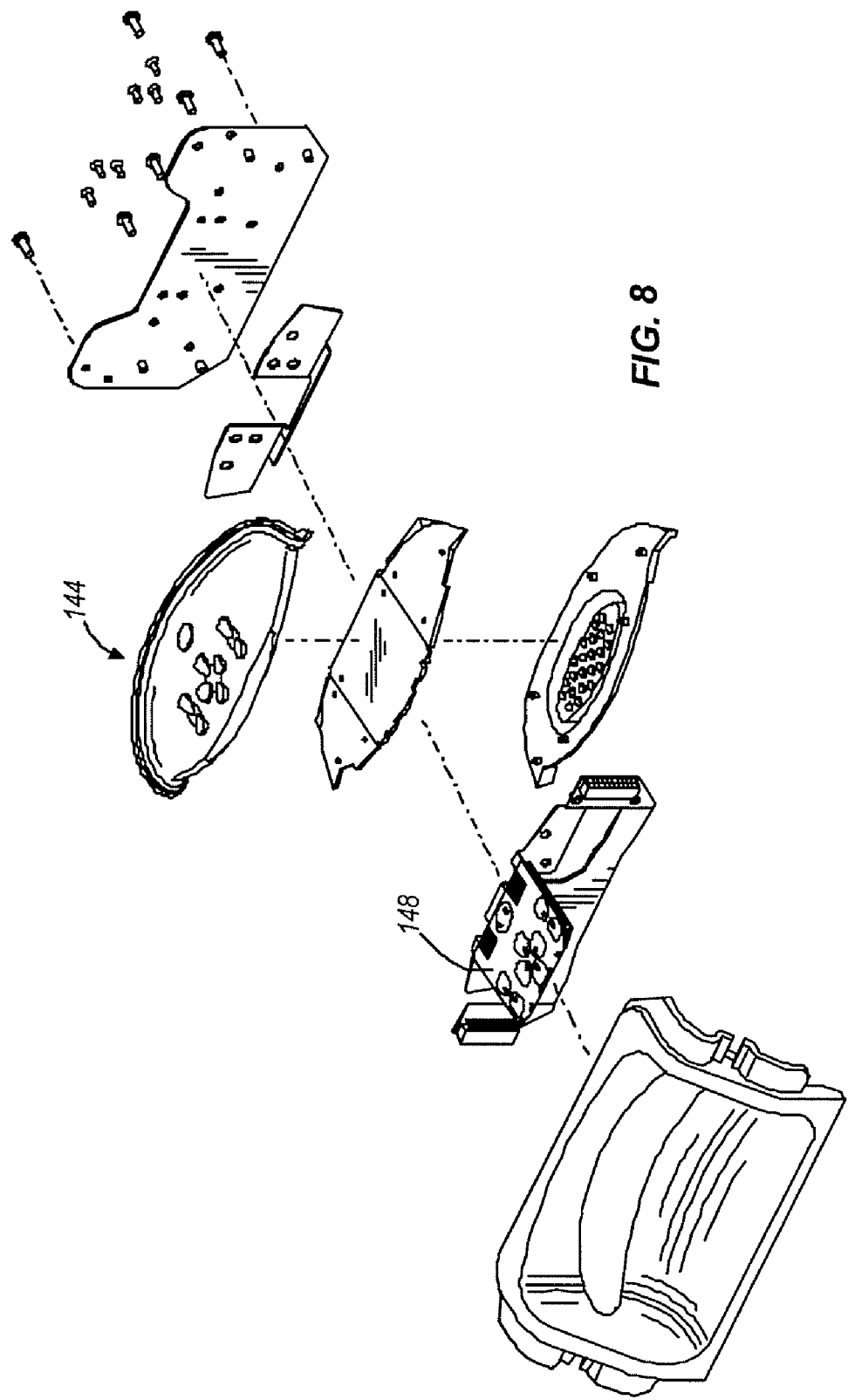
FIG. 8 is an exploded view of the keypad of FIG. 7.
Figure 9:
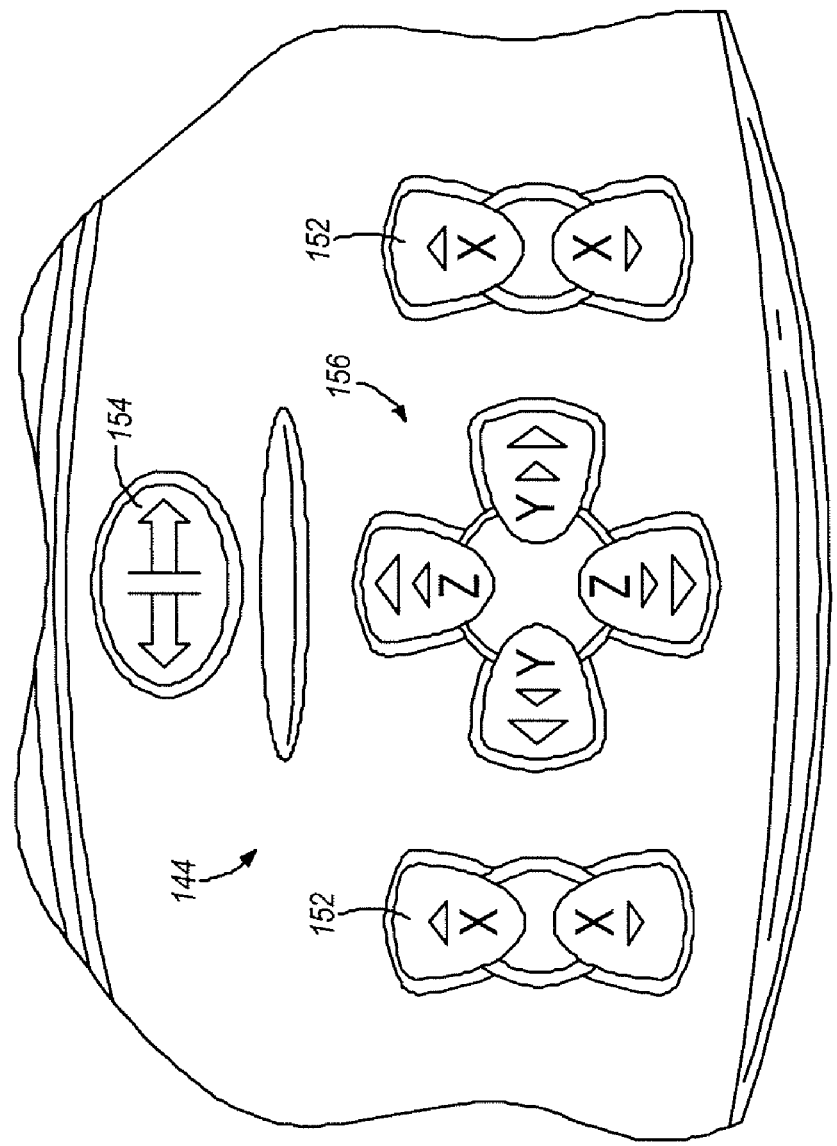
FIG. 9 is a front view of the keypad of FIG. 7, illustrating the control buttons in greater detail
Figure 10:
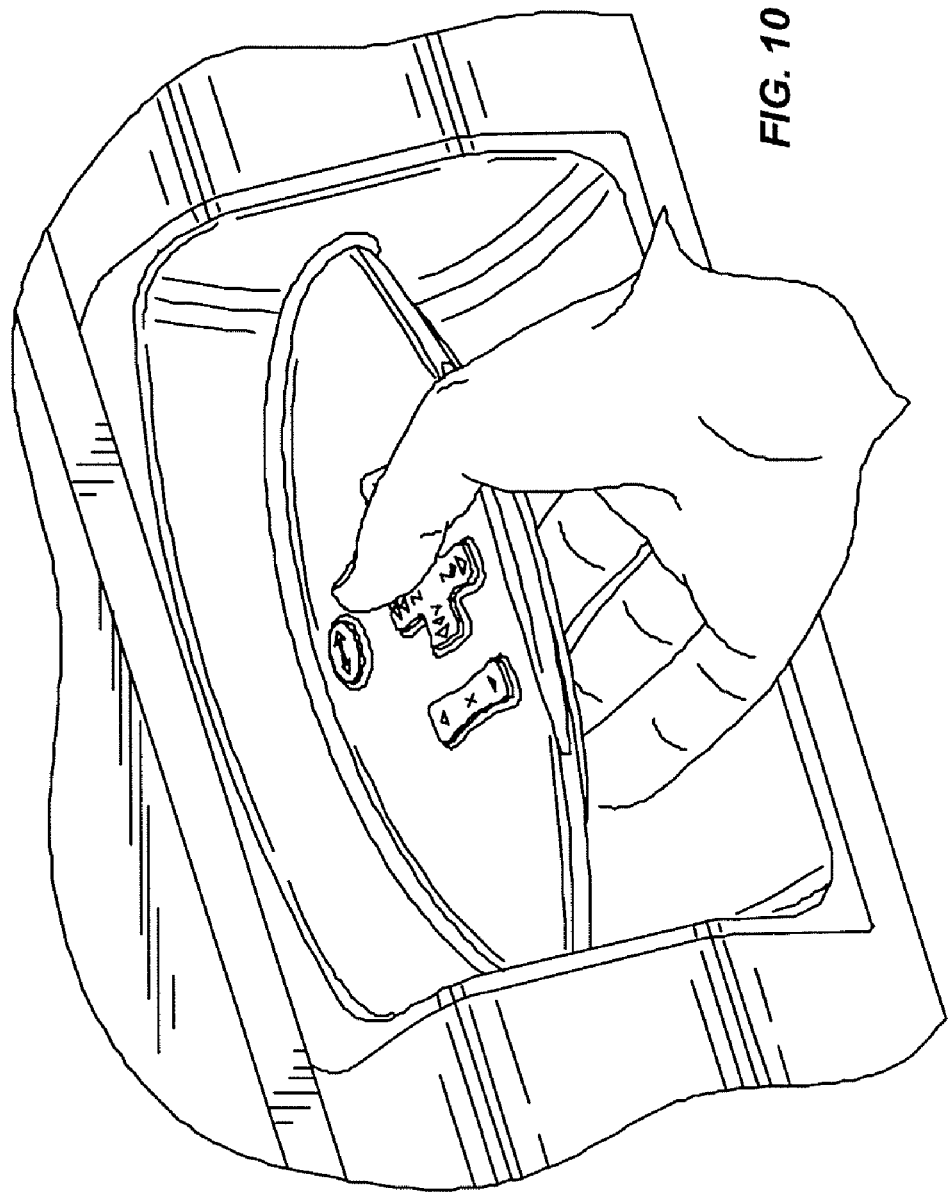
FIG. 10 is a perspective view of the keypad of FIG. 7, illustrating operation of the buttons by the operator of the patient support device
Figure 11:
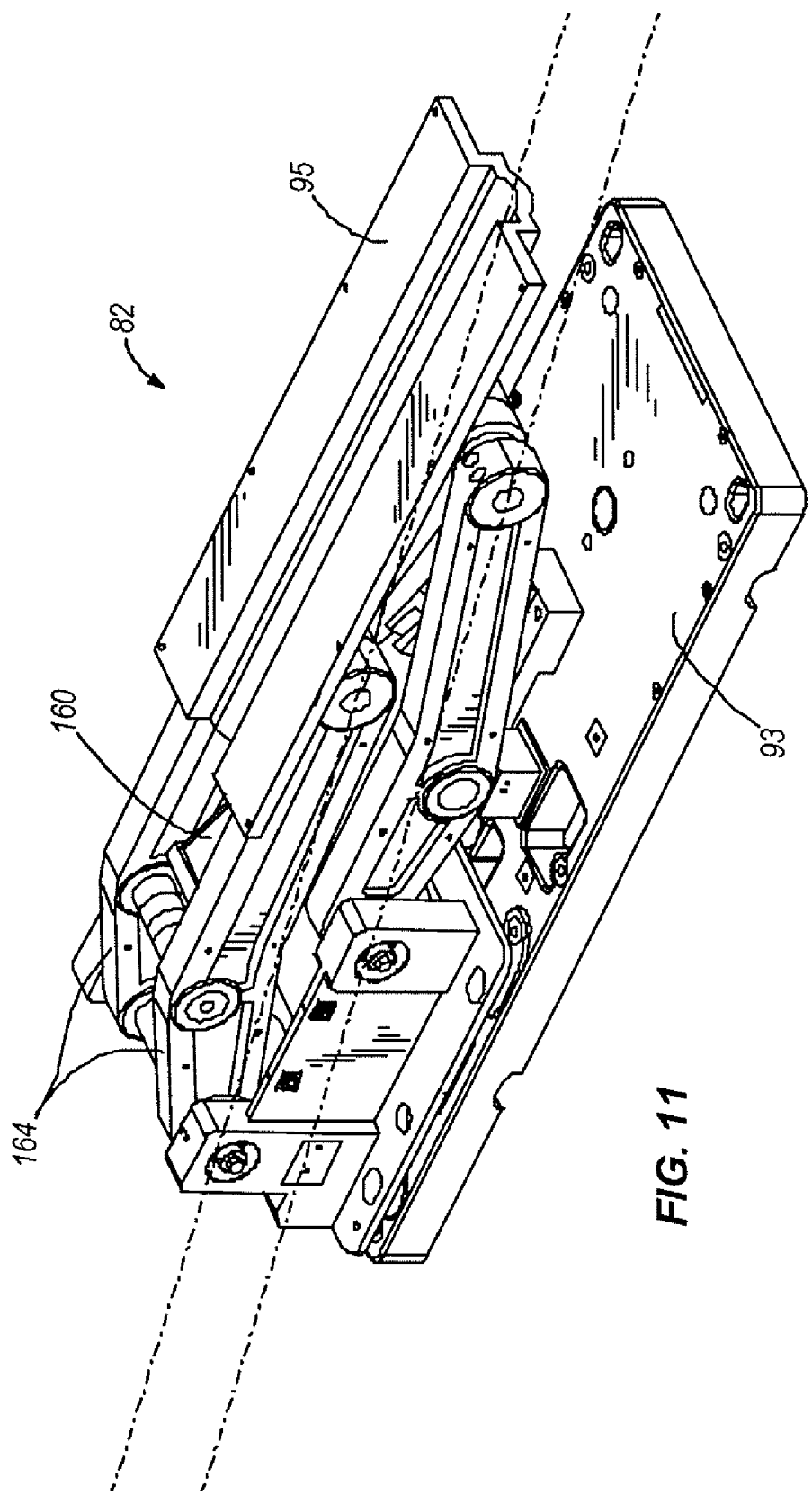
FIG. 11 is a perspective view of the patient support device of FIG. 3, shown in the lowered position.
Figure 12:
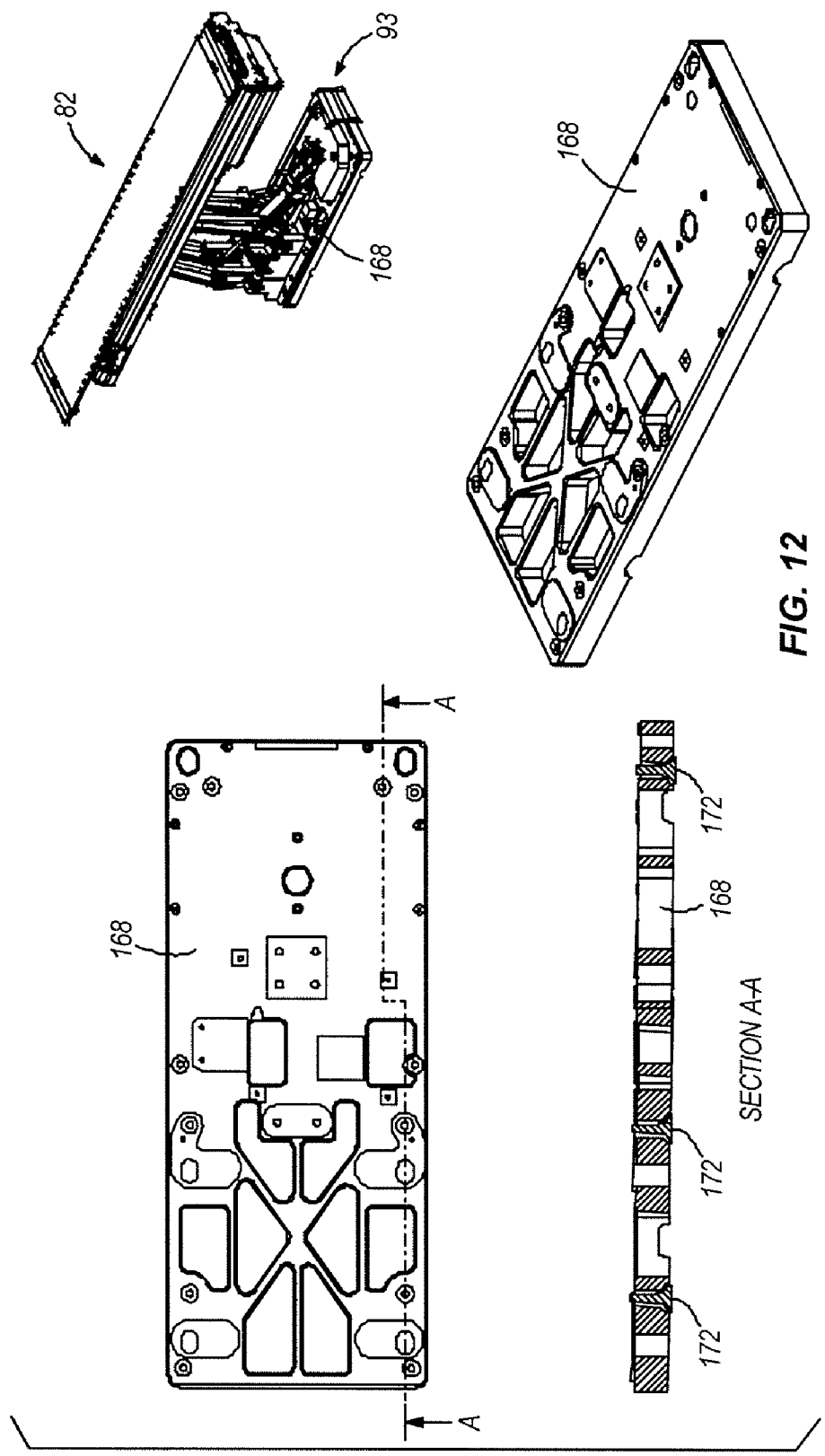
FIG. 12 illustrates a riser of the patient support device of FIG. 3.

With reference to FIGS. 3 and 11, the couch 82 according to the present invention, includes a lowering mechanism 160 with resistive braking capabilities to allow for the controlled lowering of the table assembly 92 in powered off situations. More specifically, the lowering mechanism 160 utilizes an electro-mechanical roller screw configuration. This configuration has the benefits of being less expensive to implement, being more reliable (e.g., the reliability of a roller screw implementation), and allowing for more accurate control of couch motion and position than the conventional hydraulic lifting mechanisms. The lowering mechanism 160 as described herein is responsible for motion in the vertical direction (i.e., the Z direction).

The lowering mechanism 160 includes power braking resistors to dissipate energy from a motor 170 to control the downward motion of the table assembly 92. The braking resistors act as a damping or deceleration device, taking the energy output of the motor 170 and allowing for controlled lowering of the table assembly 92, even in the powered off situation. This allows for regulated control of a free running motor that provides linear motion of the mechanical system under nonlinear external loads, even if the power to the system is interrupted. The braking resistors are designed so that no matter the load on the table assembly 92, the downward speed of the table assembly 92 remains the same. By keeping the speed constant, even with a dynamic load, control of the motion is achieved.

Using the lowering mechanism 160, the motor 170 becomes a generator during the lowering process of the table assembly 92 (i.e., if the power is uncontrolled, the power and speed increase as the couch drops). To prevent this, there needs to be a change in the load resistance applied proportionately to the power generated. When the generator has too high of a load, it begins braking. The effective value of the resistance is changed by connecting and disconnecting a power resistor. If the power resistor were constantly applied to the lowering mechanism 160, the speed of the table assembly 92 would increase as the table assembly 92 is lowered (simulating a free fall) that could cause the table assembly 92 to crash at the bottom of the path of motion. By alternating the connection of the power resistor to the lowering mechanism 160, the table assembly 92 is protected from crashing. By applying a non-linear load to the lowering mechanism 160, the speed drop of the table assembly 92 is linear such that the resistance linearizes what was previously non-linear motion. The frequency with which the power resistor is connected to the lowering mechanism 160 changes the effective resistance within the braking circuitry.

The lowering mechanism 160 also includes support arms 164 that couple the table assembly 92 to a riser 168 of the base 93. As shown in the illustrated embodiment, the lowering mechanism 160 includes two pairs of support arms 164, with each arm 164 within a pair of arms being parallel to the other. As the table assembly 92 is raised and lowered, a longitudinal axis of each arm 164 within a pair remains parallel to the other arm, and a plane $P_1$ formed by the longitudinal axis of one pair of arms does not intersect a plane $P_2$ formed by the longitudinal axis of the other pair of arms.

Movement of the table assembly 92 in the Z axis, as described in some detail above, utilizes an electromechanical roller screw. The Z axis motion is controlled by a dual feedback mechanism. Incremental feedback is provided by the roller screw, and a direct drive encoder looks at angle and provides absolute feedback. All axes of the couch 82 have step-move capabilities due to their control mechanisms. In the Z direction, doing a step-move will correct for cobra motion in the Y axis direction.

Figure 13:
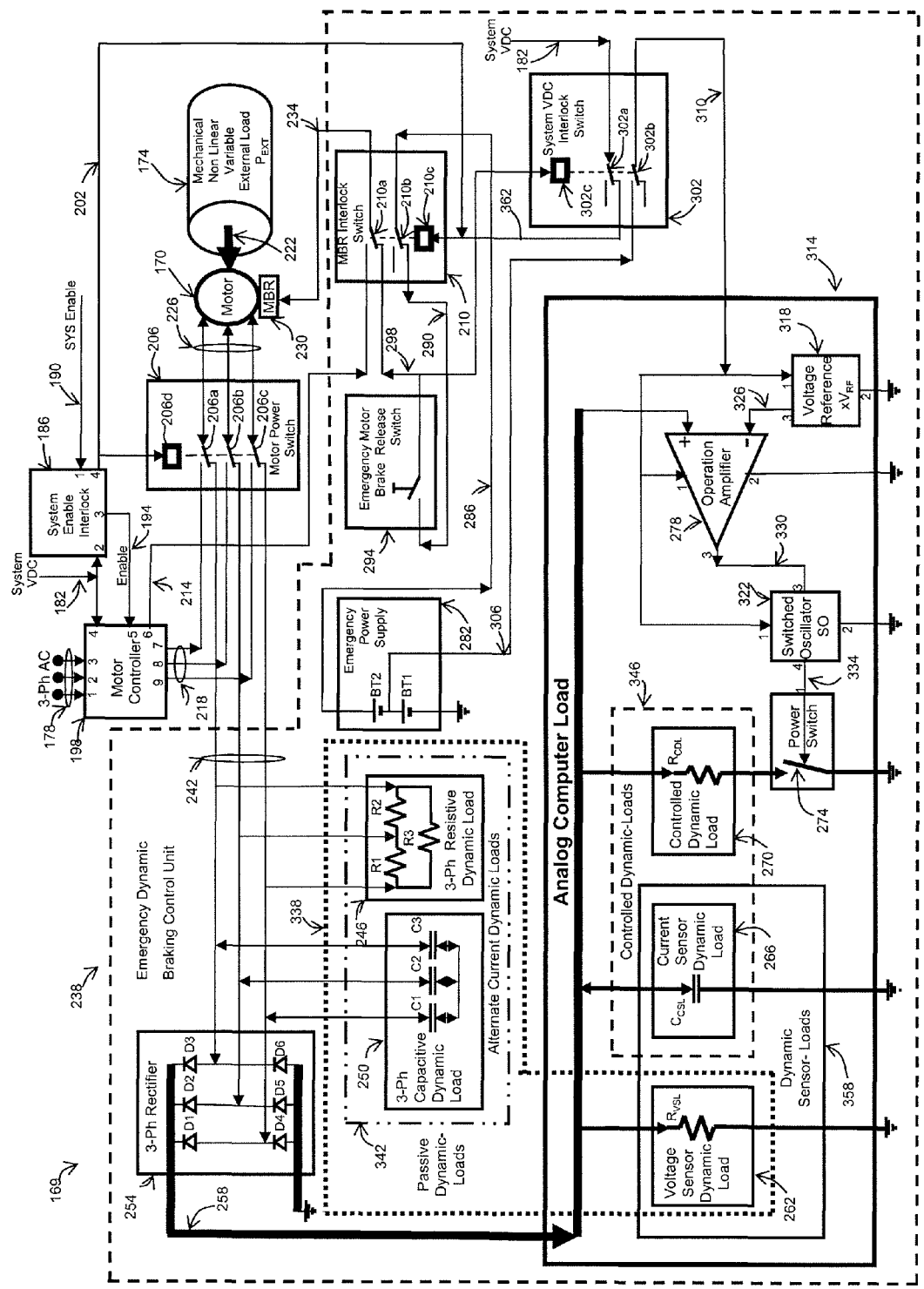
FIG. 13 is a schematic view of an exemplary motor control system according to the present invention.
Figure 14:
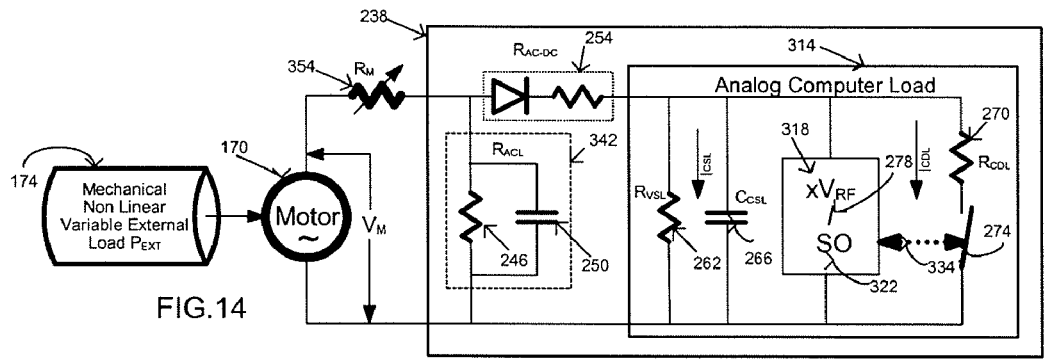
FIG. 14 is an equivalent schematic illustrating a method of an exemplary motor control system with the motor working in free running mode as motor-turned-generator under the control of an emergency dynamic braking control unit according to the present invention.
Figure 21:
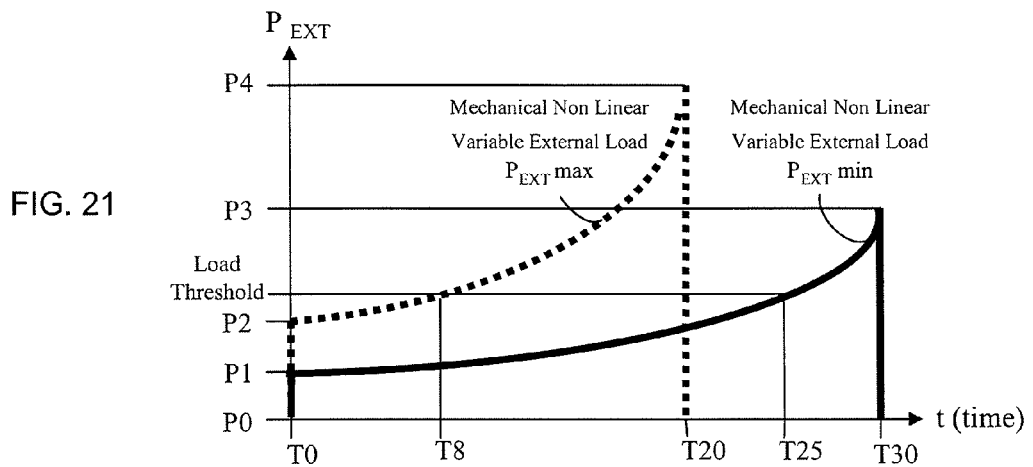
FIG. 21 is a graph illustrating various curves of the mechanical non-linear variable external load.

The lowering mechanism 160 includes a motor control system 169 as illustrated in FIG. 13. The motor control system 169 includes the motor 170 and motor controller 198, which controls the motor 170 in both the regular mode and in the case of the free-running motor-turned-generator mode under the mechanical non-linear variable external load $P_{EXT}$ 174 when the main power (3-Phase AC bus 178 and system VDC bus 182) to the couch 82 is interrupted. FIG. 21 is a graph illustrating various curves of the mechanical non-linear variable external load 174 ($P_{EXT}$).

The motor control system 169 includes a system enable interlock 186 where pin 1 is connected to SYS enable bus 190, pin 2 is connected to system VDC bus 182, pin 3 is connected through the enable bus 194 to pin 5 of the motor controller 198, and pin 4 is connected through bus 202 to a coil 206d of a motor power switch 206 and to a coil 210c of a motor brake release (MBR) interlock switch 210.

The motor controller 198 includes pin 1, pin 2, and pin 3 connected to the 3-Ph AC bus 178, pin 4 connected to system VDC bus 182, pin 6 connected through bus 214 to normally-open contact 210a of the MBR interlock switch 210, and pin 7, pin 8, and pin 9 connected through 3-Phase Motor Controller Bus 218 to appropriate normally-open contacts 206a, 206b, 206c of the motor power switch 206.

The motor 170 is connected through a shaft 222 to the mechanical non-linear variable external load $P_{EXT}$ 174. A three-phase power bus 226 connects the motor 170 to the appropriate common contacts 206a, 206b, 206c of the motor power switch 206. The motor 170 includes a motor brake release (MBR) 230 connected through bus 234 to common contact 210a of the MBR interlock switch 210.

The motor control system 169 also includes an emergency dynamic braking control unit 238 connected through 3-Phase Power bus 242 to appropriate normally-closed contacts 206a, 206b, and 206c of the motor power switch 206. A delta connected 3-Phase resistive dynamic load 246 is connected to appropriate phases of the 3-Phase power bus 242. A star connected 3-Phase capacitive dynamic load 250 is connected to appropriate phases of the 3-Phase power bus 242. A 3-Phase rectifier 254, with common points of diodes D1-D4, D2-D5, and D3-D6, is connected to appropriate phases of the 3-Phase Power bus 242. The common points of the diodes D4, D5, D6 are connected to ground and the common points of the diodes D1, D2, D3 are connected to the power-control-sensor bus 258.

The power-control-sensor bus 258 is connected to a voltage sensor dynamic load 262 ($R_{VSL}$), and the other side of the $R_{VSL}$ is connected to ground. The power-control-sensor bus 258 is also connected to a current sensor dynamic load 266 ($C_{CSL}$), and the other side of the $C_{CSL}$ is connected to ground. The power-control-sensor bus 258 is also connected to a controlled dynamic load 270 ($R_{CDL}$). The other side of the $R_{CDL}$ is connected to a normally-open contact of a power switch 274, while the common contact of the power switch 274 is connected to ground. The power-control-sensor bus 258 also is connected to a positive input of an operation amplifier 278.

The emergency dynamic braking control unit 238 includes an emergency power supply 282, which contains two rechargeable batteries BT1, BT2 connected in series. The negative lead of the battery BT1 is connected to ground and the positive lead of the battery BT2 is connected through bus 286 to common contact 210b of the MBR interlock switch 210. The normally closed contact 210b is connected through bus 290 to the normally open contact of an emergency motor brake release switch 294. The common contact of this switch 294 is connected through bus 298 to coil 302c of a system VDC interlock switch 302 and to normally closed contact 210a of the MBR interlock switch 210. The common point of the batteries BT1 and BT2 are connected through bus 306 to normally open contact 302b of the system VDC interlock switch 302. The common contact 302a is connected to system VDC through bus 182 and normally closed contact 302a is connected to coil 210c of the MBR interlock switch 210 through bus 362. Common contact 302b is connected to bus 310, which supplies analog computer load 314 and is connected to pin 1 of a voltage reference 318, to pin 1 of the operation amplifier 278, and to pin 1 of a switched oscillator 322. The voltage reference 318 is connected by pin 2 to ground and is connected by pin 3 through bus 326 to the negative input of the operation amplifier 278. The operation amplifier 278 is connected by pin 2 to ground and is connected by pin 3 through bus 330 to pin 3 of the switched oscillator 322. The switched oscillator 322 is connected by pin 2 to ground and is connected by pin 4 through bus 334 to pin 1 of the power switch 274.

The motor 170 is initiated when it receives a signal from the 3-Phase AC power on the bus 178, system VDC on the bus 182, and SYS enable signal on the bus 190. The system enable interlock 186 initiates the motor controller 198, the motor power switch 206, the MBR interlock switch 210, and the system VDC interlock switch 302 through normally closed contact 302a. The motor controller 198 communicates with the motor 170 through the bus 218, normally open contacts 206a, 206b, 206c of the motor power switch 206, and bus 226. The motor 170 begins acting through shaft 222 on the mechanical non-linear variable external load $P_{EXT}$ 174.

The motor controller 198 also communicates with the motor brake release 230 through bus 214, normally open contact 210a, and bus 234 to disengage the motor brake release 230. When main power 3-Phase AC on bus 178 and system VDC on bus 182 are interrupted, the switches 206, 210 are disengaged and the motor brake release 230 is engaged.

The motor 170 is connected to the emergency dynamic braking control unit 238 through bus 226, normally closed contacts 206a, 206b, 206c, and through 3-Phase power bus 242. To activate the emergency mode when the mechanical non-linear variable external load $P_{EXT}$ 174 begins acting through shaft 222 on the motor 170, the user needs to push and hold the emergency motor brake release switch 294. The MBR release switch 294 is activated through bus 298 to engaged coil 302c of the system VDC interlock switch 302, and to switch 302 by contact 302a to disengaged coil 210c of the MBR interlock switch 210. The motor is reactivated when the MBR 230 is disengaged. The MBR 230 is disengaged when the MBR release switch 294 is released through bus 298, normally closed contact 210a, and bus 234. The motor 170 begins acting under external load $P_{EXT}$ 174, and the 3-Phase AC voltage from the motor 170 begins to interact with Passive Dynamic Loads 338. The motor 170 gets first two stages of dynamic braking action on the AC Dynamic Loads 342 of the Passive Dynamic Loads 338. The AC Dynamic Loads 342 includes two types of AC loads: (1) the 3-Phase Resistive Dynamic Load 246 which transfers AC energy from the motor into heat, and (2) the 3-Phase Capacitive Dynamic Load 250 which shifts AC phases from the motor 170. Both heat dissipation and phase shift increases current from the motor 170 and this current increases eddy currents in the motor 170 which affect braking action in the motor 170.

The motor 170 continuously increases speed under $P_{EXT}$ 174 until the AC voltage from the motor reaches a certain value, and then the AC voltage begins rectification by 3-Phase Rectifier 254. The rectified AC voltage begins a third stage in the DC passive dynamic braking on the Voltage Sensor Dynamic Load 262 ($V_{VSL}$) of the Passive Dynamic Loads 338. The motor 170 proceeds to increase speed under $P_{EXT}$ 174 and the DC voltage increases too, until a certain value is reached, and then the Analog Computer Load 314 begins to control the dynamic braking action. The Analog Computer Load 314 is supplied by two sources: (1) the Emergency Power Supply 282 through BT1, through bus 306, normally open contact 302b, and bus 310, and (2) motor 170 through bus 226, normally closed contacts 206a, 206b, 206c, bus 242, 3-Phase Rectifier 254, and Power-Control-Sensor Bus 258.

There are two conditions of operation of the motor control system 169:

Condition 1:

$$xV_{RF} > V_{VSL} \quad (1)$$

Only the Passive Dynamic Loads 338 are working. And time charge $t_{CH}$ of the capacitor $C_{CSL}$ 266 will have an infinite value.

Condition 2:

$$xVRF < V_{VSL} \quad (2)$$

Figure 22:
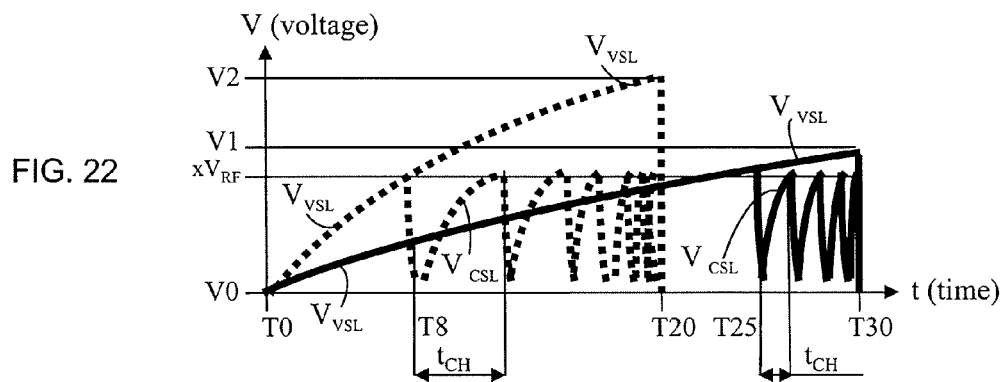
FIG. 22 is a graph illustrating the curves of the equivalent voltage source $V_{VSL}$, voltages $V_{CSL}$, and time charge $t_{CH}$ on the current sensor load $C_{CSL}$ under different values of external loads $P_{EXT}$.

The Passive Dynamic Loads 338 and the Controlled Dynamic Loads 346 begin working together, and the time charge $t_{CH}$ of the capacitor $C_{CSL}$ 266 operates up to a value of the voltage $xV_{RF}$ 318. This value of the time charge $t_{CH}$ will be inversely proportional to a value of the load $P_{EXT}$ 174. FIG. 22 is a graph illustrating the curves of the equivalent voltage source $V_{VSL}$, voltages $V_{CSL}$, and time charge $t_{CH}$ on the current sensor load $C_{CSL}$ under different values of external loads $P_{EXT}$.

Figure 15:
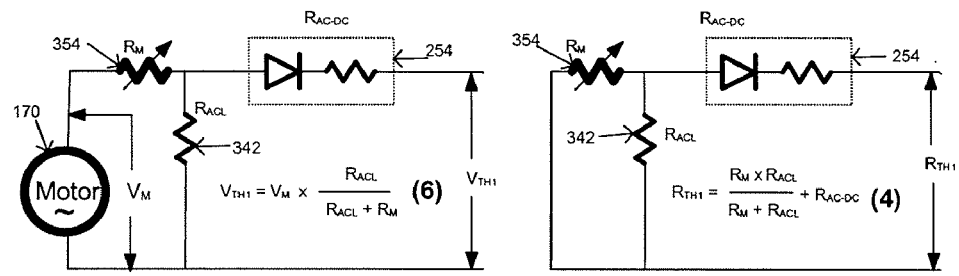
FIG. 15 is an equivalent schematic illustrating a method of an exemplary Thevenin equivalent of the motor AC voltage source with conversion to DC voltage source $V_{TH1}$.
Figure 16:
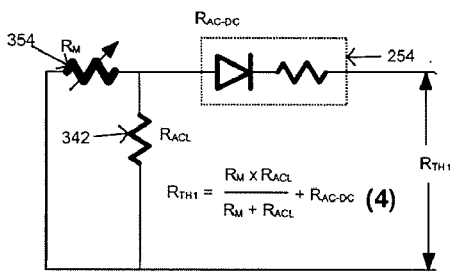
FIG. 16 is an equivalent schematic illustrating a method of an exemplary Thevenin equivalent resistance of the $R_M$, $R_{AC\text{-}DC}$, and $R_{ACL}$ with conversion to $R_{TH1}$.
Figure 17:
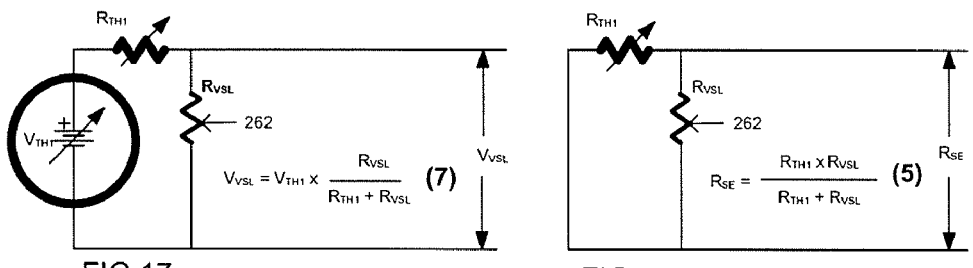
FIG. 17 is an equivalent schematic illustrating a method of an exemplary Thevenin equivalent of the DC voltage source $V_{TH1}$ with conversion to voltage source $V_{VSL}$.
Figure 18:
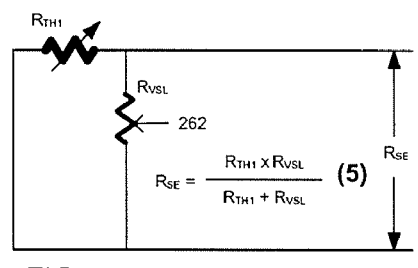
FIG. 18 is an equivalent schematic illustrating a method of an exemplary Thevenin equivalent resistance of the $R_{TH1}$ and $R_{VSL}$ with conversion to $R_{SE}$ sensor equivalent.
Figure 19:
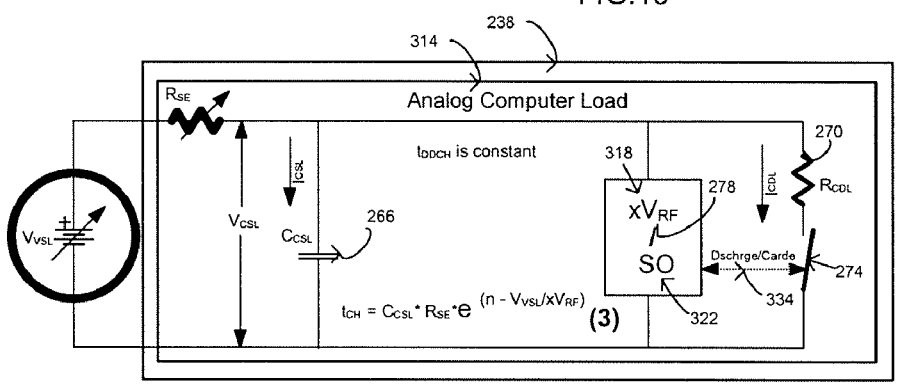
FIG. 19 is a schematic illustrating a method of an exemplary motor control system when the motor is working in free running mode under control of the emergency dynamic braking control unit when an analog computer load is active.
Figure 20:
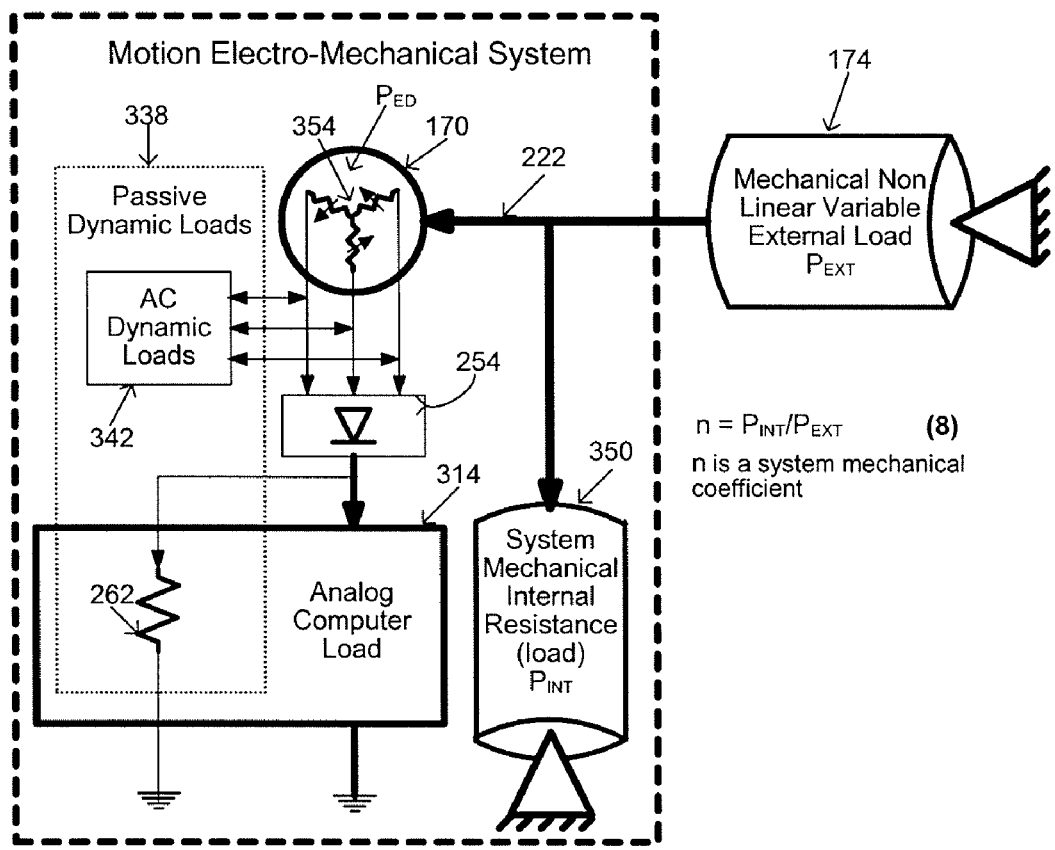
FIG. 20 is a diagram illustrating an exemplary force distribution between external $P_{EXT}$ and system mechanical $P_{INT}$ and electrodynamic $P_{ED}$ resistance forces.

The time charge $t_{CH}$ of the capacitor $C_{CSL}$ 266 up to value of the voltage $xV_{RF}$ is illustrated in FIG. 19 and determined by $$t_{CH} = C_{CSL} * R_{SE} * e^{\left(n - \frac{V_{VSL}}{xV_{RF}}\right)} \quad (3)$$

where $R_{SE}$ is the resistance of the sensor equivalent, which is calculated by formula (4) illustrated in FIG. 16 and formula (5) illustrated in FIG. 18. $R_{SE}$ represents the internal resistance of the motor 170 with relationship to the $P_{EXT}$ 174; and $V_{VSL}$ is the Thevenin voltage source equivalent of the Motor 170 which is calculated by formula (6) illustrated in FIG. 15 and formula (7) illustrated in FIG. 17.

n is determined by formula (8) (provided below) illustrated in FIG. 20.

$$n = \frac{P_{INT}}{P_{EXT}} \quad (8)$$

where n is a mechanical system coefficient, n=0 . . . 1 (n is a positive number)

$P_{INT}$ is a system mechanical internal resistance 350

$P_{EXT}$ is a mechanical non-linear variable external load 174

$xV_{RF}$ is the value of the Voltage Reference 318 x is an adjusting coefficient which allows adjustment of the Emergency Dynamic Braking Control Unit 238 for different motors and different values of the braking speed control.

Figure 23:
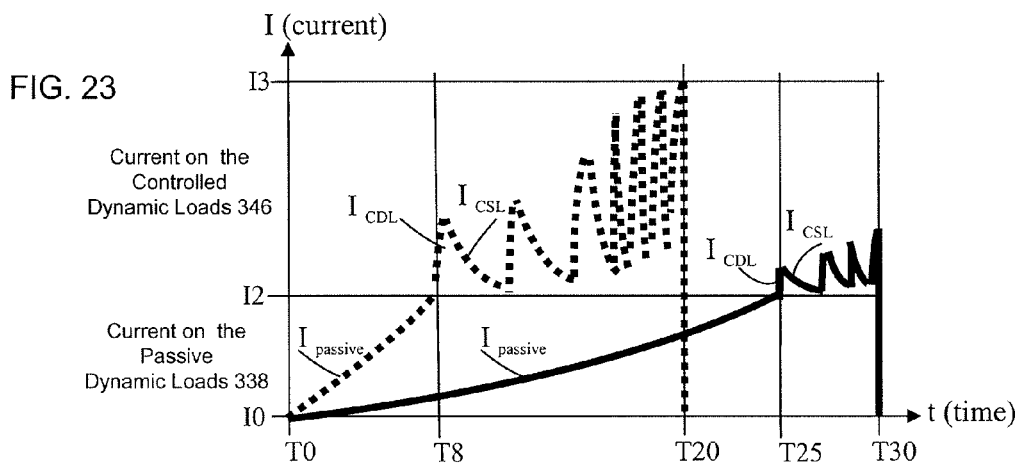
FIG. 23 is a graph illustrating the current on the passive dynamic loads and current on the controlled dynamic loads under different values of external loads $P_{EXT}$.

FIG. 23 is a graph illustrating the current on the passive dynamic loads and current on the controlled dynamic loads under different values of external loads $P_{EXT}$. $I_{CSL}$, illustrated in FIG. 19, of the Current Sensor Dynamic Load 266 is directly proportional to the value of the $P_{EXT}$ 174

$$I_{CSL} \| P_{EXT} \quad (9)$$

The operation amplifier 278 controls changes of the voltage on the Capacitor Sensor Dynamic Load ($C_{CSL}$) 262 and compares it with the value of the voltage on the Voltage Reference ($xV_{RF}$) 318. When the voltage $V_{CSL}$ on capacitor $C_{CSL}$ 262 becomes equal to or higher than the value on the $xV_{RF}$ 318, the operation Amplifier 278 starts Switched Oscillator 322. The Switched Oscillator 322 is switched with a predetermined time $t_{DDCH}$ of the Power Switch 274. The Power Switch 274 connects the Controlled Dynamic Load 270 to ground, which begins the fourth stage of the dynamic braking action of the motor 170 on the Controlled Dynamic Load 270. The Controlled Dynamic Load 270 discharges Capacitor $C_{CSL}$ of the Current Sensor Dynamic Load 266. The predetermined time discharge $t_{DDCH}$ should be greater than the time constant of the discharge capacitor $C_{CSL}$ $$t_{DDCH} > \tau_{DCH} = C_{CSL} * R_{CDL} * \left(1 + \frac{R_{DCL}}{R_{SE}}\right) \quad (10)$$

During the predetermined time $t_{DDCH}$ that Operation Amplifier 278 controls the voltage on the Capacitor Sensor Dynamic Load 262, the operation amplifier 278 continuously compares the $C_{CSL}$ voltage with value of the voltage on the Voltage Reference 318 ($xV_{RF}$) until the voltage $xV_{RF}$ becomes equal to or higher than the value $C_{CSL}$ 262. When the predetermined time $t_{DDCH}$ elapses, the Switched Oscillator 322 disconnects Power Switch 274, which disconnects $R_{CDL}$ 270 from ground, which begins the fifth stage of the dynamic braking action of the motor 170 on the Current Sensor Dynamic Load 266 ($C_{CSL}$).

The instantaneous current $I_{INST}$ through the capacitor of the Current Sensor Dynamic Load 266 ($C_{CSL}$) is determined by:

$$I_{INST} = C_{CSL} * \frac{V_{CSL}}{C_{CSL}} * R_{SE} * e^{\left(n - \frac{V_{VSL}}{xV_{RF}}\right)} \quad (11)$$

Figure 24:
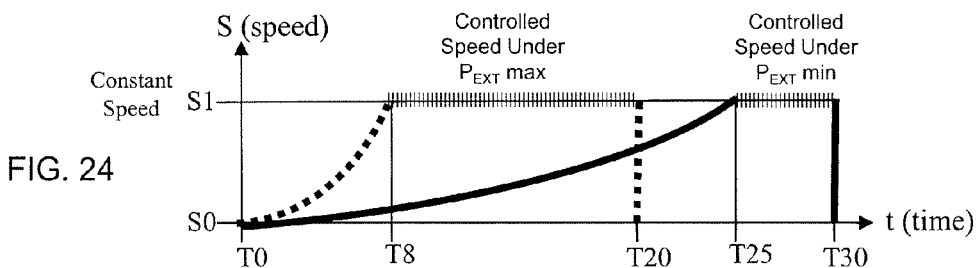
FIG. 24 is a graph illustrating a method of the motor speed control under different values of external loads $P_{EXT}$.

When the voltage on the Current Sensor Dynamic Load 266 ($C_{CSL}$) again becomes equal to or greater than the value on the Voltage Reference 318 ($xV_{RF}$), the Operation Amplifier 278 restarts the Switched Oscillator 322. The Switched Oscillator 322 is switched with predetermined time $t_{DDCH}$ of the Power Switch 274. The Power Switch 274 is connected to Controlled Dynamic Load 270 to ground, which again begins the fourth stage of the dynamic braking action of the motor 170 on the Controlled Dynamic Load 270. The Controlled Dynamic Load 270 discharges the capacitor of the Current Sensor Dynamic Load 266 ($C_{CSL}$). That cycling will continue on the shaft 222 of the motor 170 and the mechanical non-linear variable external load $P_{EXT}$ 174 and during that cycle the Emergency Dynamic Braking Control Unit 238 will manage linear motion of the whole mechanical system. FIG. 24 is a graph illustrating the motor speed control under different values of external loads $P_{EXT}$.

Some of the unique features of the present invention include (1) A motor-turned-generator 170 is a source for generating braking forces and a source of information about its conditions.

(2) The load power link, the sensors link, and the control link are on the same bus 258.

(3) The voltage sensor dynamic load 262 ($V_{CSL}$) and the current sensor dynamic load 266 ($C_{CSL}$) are multifunctional:
  (a) Voltage Sensor Dynamic Load 262 ($V_{CSL}$) is the DC passive load of the system Passive Dynamic Loads 338, and the voltage sensor recognizes the internal resistance of the motor 170 like a voltage drop on itself.
  (b) Current Sensor Dynamic Load 266 ($C_{CSL}$) is a three function device: the integrator in the analog computer load 314, a current sensor, which recognizes the current value of the motor 170 as a time charge of the capacitor up to a certain value on the Voltage Reference 318 ($xV_{RF}$), and the controlled dynamic load in the analog computer load 314.

(4) The dynamic braking of the motor occurs in multiple stages:
  (a) The passive dynamic load 338 comprises the AC dynamic load 342, which includes the 3-Ph capacitive dynamic load 250 (passive braking—stage 1) and the 3-Ph resistive dynamic load 246 (passive braking—stage 2) and the DC dynamic load, which includes the voltage sensor dynamic load 262 (passive braking—stage 3).
  (b) The controlled dynamic load 346 includes the controlled dynamic load 270 (controlled braking—stage 4) and the current sensor dynamic load 266 (controlled braking—stage 5).

(6) The capacitor of the current sensor dynamic load 266 is not a reactive load with respect to the motor 170 because the capacitor is charged from the motor 170 and is discharged through a resistor(s) of the controlled dynamic load 270, which means that the capacitor does not return charged energy back to the motor 170. The capacitor continues to be non-linear load.

(7) The controlled dynamic loads 346 include a two-cycle controlled dynamic load which provides a two-cycle controlled dynamic braking action on the motor 170. The first cycle is controlled by the controlled dynamic load 270, which provides the dynamic braking action on the motor 170 and discharges the capacitor of the current sensor dynamic load 266 ($C_{CSL}$) during predetermined time $t_{DDCH}$. The second cycle is controlled by the current sensor dynamic load 266, which provides dynamic braking action on the motor 170 during the charge time $t_{CH}$ of the capacitor of the current sensor dynamic load 266.

(8) When motor 170 operates as a motor-turned-generator it has the following properties:
  (a) the motor 170 becomes a voltage source;
  (b) the internal resistance of the voltage source is variable and inversely proportional to the speed of the motor and the mechanical load on the motor. In this mode, the motor 170 works like a sensor where the voltage reflects the speed of the motor and the current reflects the mechanical load on the shaft 222 of the motor.

(9) The analog computer load 314 includes combined properties of the analog computer and the controlled dynamic loads.

Figure 25:
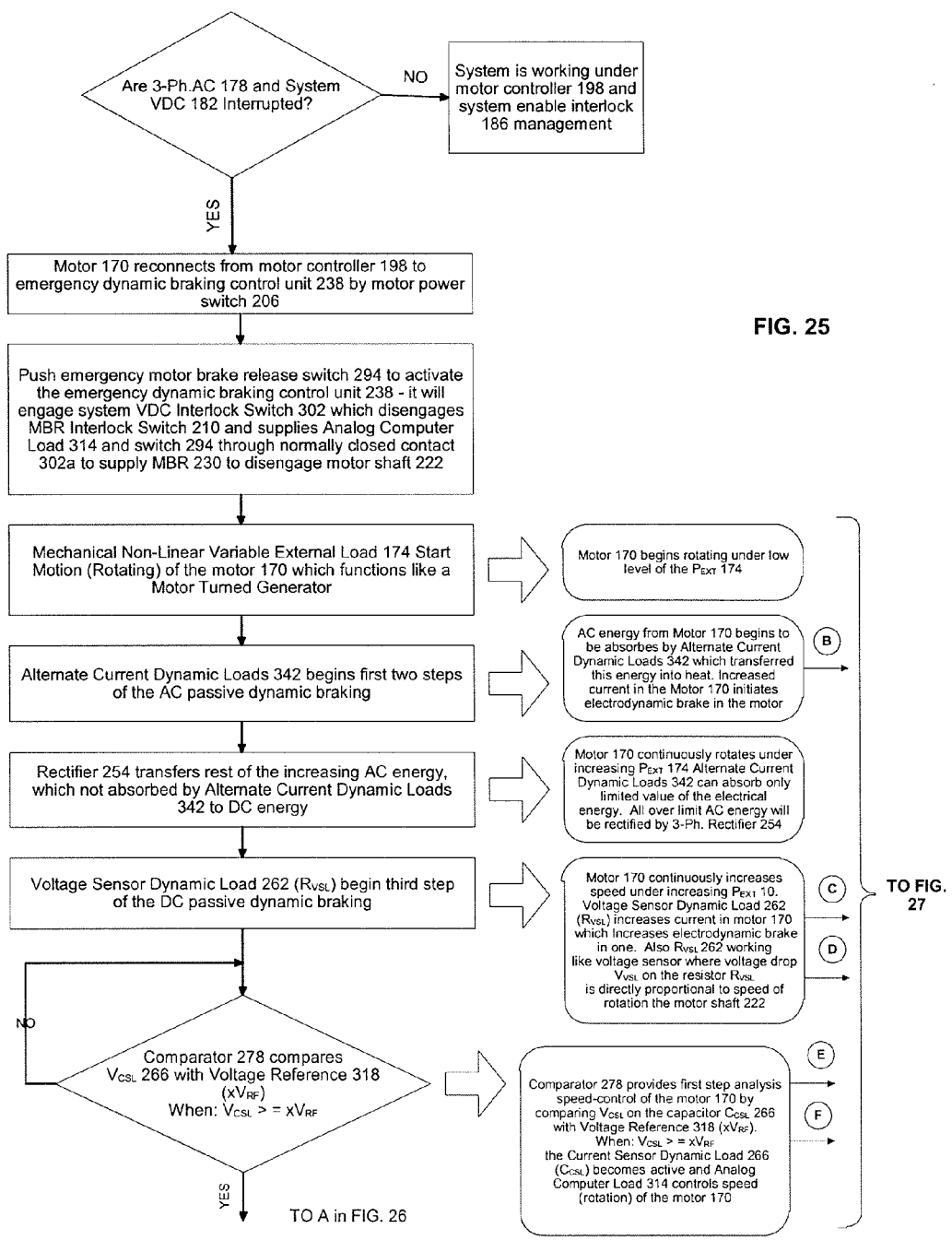
FIGS. 25-27 are a flowchart and comments illustrating an embodiment of a method of the present invention.
Figure 26:
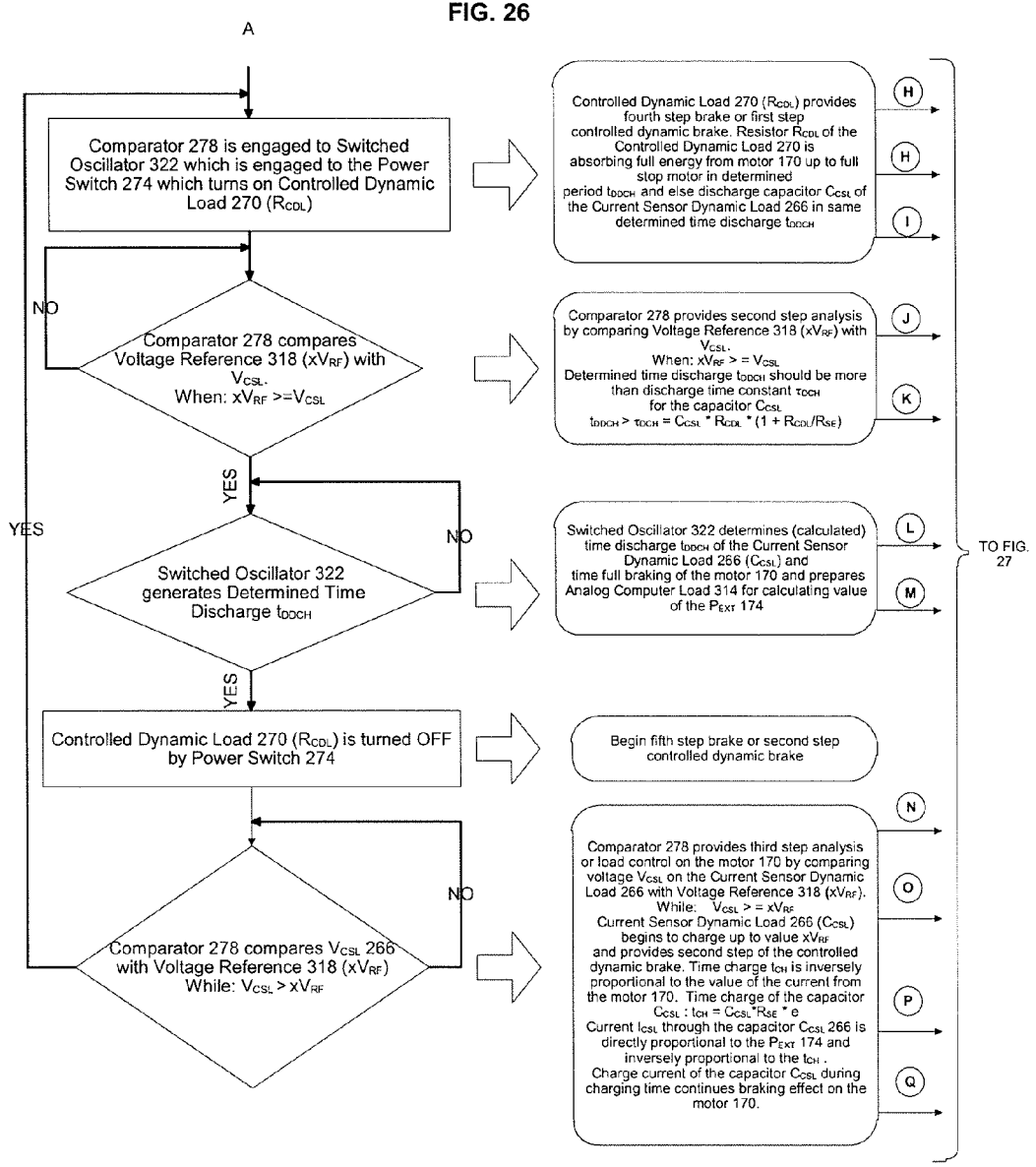
Figure 27:
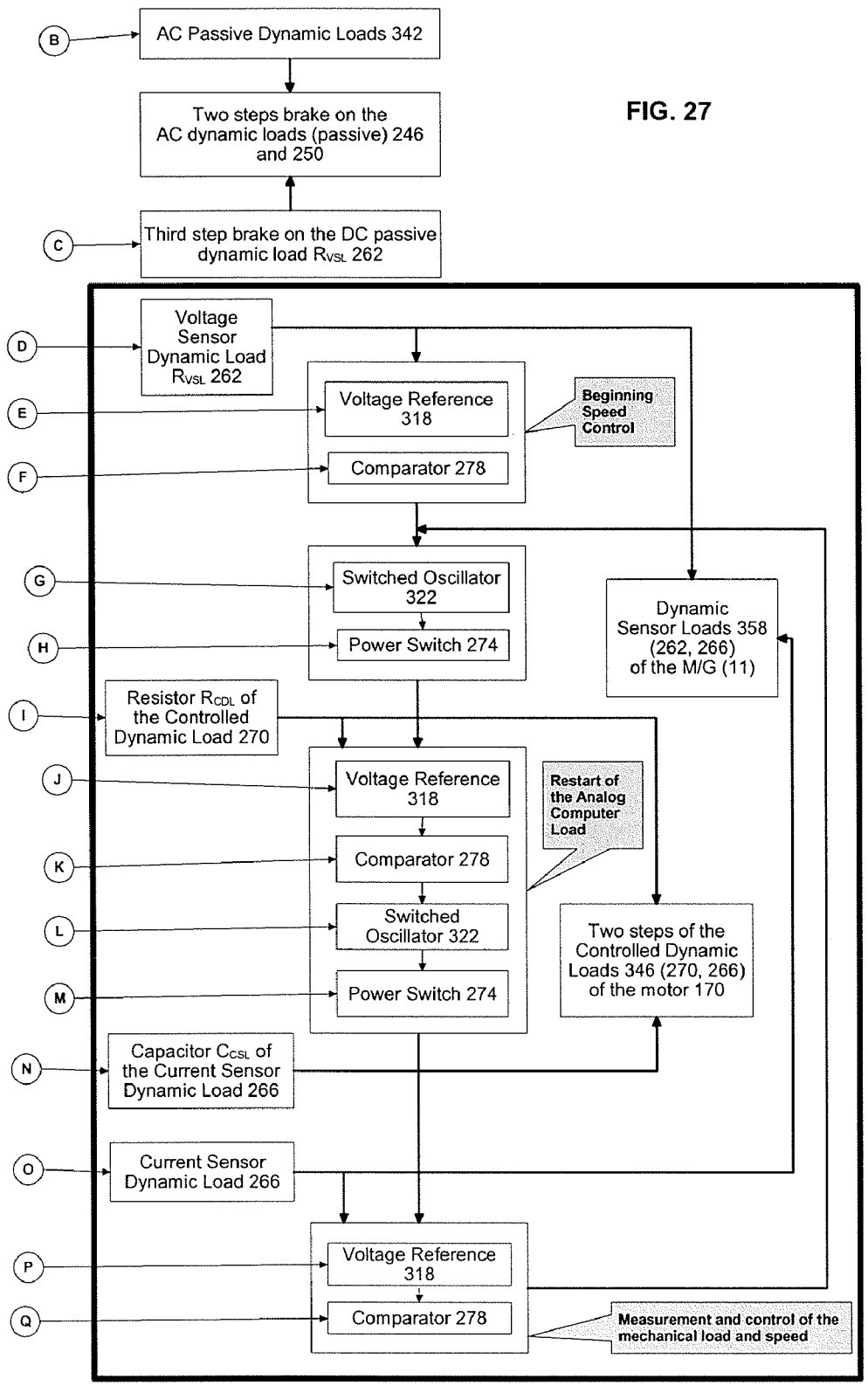

FIGS. 25-27 are a flowchart and comments illustrating an embodiment of a method of the present invention.

Additional features of this invention can be found in the following claims.

What is claimed is:

1. A method of controlling movement of a patient support device, the method comprising:
   activating an actuator assembly to move the patient support device;
   interrupting power to the actuator assembly to stop movement of the patient support device;
   activating a dynamic brake assembly after the patient support device stops moving;
   connecting the dynamic brake assembly to the actuator assembly; and
   controlling the actuator assembly with the dynamic brake assembly to move the patient support device at a substantially constant velocity.

2. The method of claim 1 further comprising activating a switch when the power to the actuator assembly is interrupted.

3. The method of claim 2 further comprising releasing the switch to connect the dynamic brake assembly to the actuator assembly.

4. The method of claim 1 wherein the actuator assembly receives AC power to vertically raise the patient support device.

5. The method of claim 4 wherein the actuator assembly receives AC power when the dynamic brake assembly is connected to the actuator assembly.

6. The method of claim 5 wherein the actuator assembly includes a motor, and wherein the motor increases speed while an AC voltage level on the motor reaches a predetermined value and wherein the AC power is rectified to DC power after the AC voltage level on the motor reaches the predetermined value.

7. The method of claim 6 wherein the motor continues to increase in speed under the application of the DC power until a predetermined DC voltage value is reached.

8. The method of claim 1 wherein the dynamic brake assembly further includes an analog computer load coupled to the rectification module.

9. The method of claim 8 wherein the analog computer load is activated when the DC voltage reaches a predetermined value.

10. The method of claim 9 wherein the dynamic brake assembly further includes a secondary power supply, and wherein the secondary power supply provides power to the analog computer load.

11. The method of claim 1 wherein the actuator assembly is configured to move the patient support device in a substantially vertical direction.

12. The method of claim 11 wherein the actuator assembly is controlled with the dynamic brake assembly to vertically lower the patient support device at a substantially constant velocity.

13. A patient support device comprising:
   a table configured to support a patient;
   an actuator assembly electrically coupled to and operable to control motion of the table, the actuator assembly including a motor and a brake;
   a controller electrically coupled to the actuator assembly, the controller operable to generate a signal to activate the brake when power to the actuator assembly is interrupted; and
   a dynamic brake assembly electrically coupled to the actuator assembly and the controller, the dynamic brake assembly operable upon deactivation of the brake, the dynamic brake assembly including
      a passive dynamic load module electrically coupled to the motor to increase speed of the motor, a rectification module electrically coupled to the motor and operable to convert AC voltage to DC voltage when the AC voltage reaches a predetermined value, a controlled dynamic load module electrically coupled to the passive dynamic load module, and a switch operable to deactivate the brake and electrically couple the controlled dynamic load module and the actuator assembly to control a braking operation of the motor.

14. The patient support device of claim 13 wherein the motor is operable to control a substantially vertical motion of the table.

15. The patient support device of claim 13 wherein the passive dynamic load module includes a capacitive dynamic load module and a resistive dynamic load module.

16. The patient support device of claim 15 wherein the passive dynamic load module further includes a voltage sensor dynamic load module.

17. The patient support device of claim 16 wherein the voltage sensor dynamic load module is operable to receive the DC voltage on the motor from the rectification module.

18. The patient support device of claim 13 wherein the controlled dynamic load module includes a current sensor dynamic load and a controlled dynamic load.

* * * * *